US010453553B2

(12) United States Patent
Chen et al.

(10) Patent No.: US 10,453,553 B2
(45) Date of Patent: Oct. 22, 2019

(54) DRUG DISCOVERY METHODS

(71) Applicant: QIAGEN Redwood City, Inc., Redwood City, CA (US)

(72) Inventors: Richard O. Chen, Redwood City, CA (US); Raymond J. Cho, San Mateo, CA (US); Ramon M. Felciano, San Francisco, CA (US); Bret Holley, New York, NY (US); Viresh Patel, San Francisco, CA (US); Daniel R. Richards, Palo Alto, CA (US); Sushma Selvarajan, Mountain View, CA (US); Keith Steward, The Woodlands, TX (US); Sara Schneider, South San Fransisco, CA (US)

(73) Assignee: QIAGEN Redwood City, Inc., Redwood City, CA (US)

( * ) Notice: Subject to any disclaimer, the term of this patent is extended or adjusted under 35 U.S.C. 154(b) by 480 days.

(21) Appl. No.: 13/914,419

(22) Filed: Jun. 10, 2013

(65) Prior Publication Data
US 2014/0121120 A1 May 1, 2014

Related U.S. Application Data

(63) Continuation of application No. 10/502,420, filed as application No. PCT/US03/03006 on Feb. 3, 2003, now Pat. No. 8,489,334.

(60) Provisional application No. 60/421,772, filed on Oct. 29, 2002, provisional application No. 60/353,176, filed on Feb. 4, 2002.

(51) Int. Cl.
G16B 20/00 (2019.01)
G16B 5/00 (2019.01)
G16B 25/00 (2019.01)
G16B 40/00 (2019.01)
G16B 45/00 (2019.01)
G16B 50/00 (2019.01)

(52) U.S. Cl.
CPC ............. G16B 20/00 (2019.02); G16B 5/00 (2019.02); G16B 25/00 (2019.02); G16B 40/00 (2019.02); G16B 45/00 (2019.02); G16B 50/00 (2019.02)

(58) Field of Classification Search
None
See application file for complete search history.

(56) References Cited

U.S. PATENT DOCUMENTS

| | | |
|---|---|---|
| 5,317,507 A | 5/1994 | Gallant |
| 5,371,807 A | 12/1994 | Register et al. |
| 5,377,103 A | 12/1994 | Lamberti et al. |
| 5,398,183 A | 3/1995 | Elliott |
| 5,418,971 A | 5/1995 | Carlson |
| 5,625,721 A | 4/1997 | Lopresti et al. |
| 5,625,814 A | 4/1997 | Luciw |
| 5,794,050 A | 8/1998 | Dahlgren et al. |
| 5,963,966 A | 10/1999 | Mitchell et al. |
| 5,976,842 A | 11/1999 | Wurst |
| 6,023,659 A | 2/2000 | Seilhammer et al. |
| 6,038,560 A | 3/2000 | Wical |
| 6,052,714 A | 4/2000 | Miike et al. |
| 6,067,548 A | 5/2000 | Cheng |
| 6,101,488 A | 8/2000 | Hayashi et al. |
| 6,115,640 A | 9/2000 | Tarumi |
| 6,154,737 A | 11/2000 | Inaba et al. |
| 6,226,377 B1 | 5/2001 | Donaghue, Jr. |
| 6,236,987 B1 | 5/2001 | Horowitz et al. |
| 6,263,335 B1 | 7/2001 | Paik et al. |
| 6,292,796 B1 | 9/2001 | Drucker et al. |
| 6,308,170 B1 | 10/2001 | Balaban |
| 6,345,235 B1 | 2/2002 | Edgecombe et al. |
| 6,370,542 B1 | 4/2002 | Kenyon |
| 6,424,980 B1 | 7/2002 | Iizuka et al. |
| 6,442,566 B1 | 8/2002 | Atman et al. |
| 6,470,277 B1 | 10/2002 | Chin et al. |
| 6,487,545 B1 | 11/2002 | Wical |
| 6,498,795 B1 | 12/2002 | Zhang et al. |
| 6,523,025 B1 | 2/2003 | Hashimoto et al. |
| 6,554,705 B1 | 4/2003 | Cumbers |
| 6,598,043 B1 | 7/2003 | Baclawski |
| 6,741,976 B1 | 5/2004 | Tuzhilin |
| 6,741,986 B2 | 5/2004 | Cho et al. |
| 6,772,160 B2 | 8/2004 | Cho et al. |
| 6,904,423 B1 | 6/2005 | Nicolaou et al. |
| 7,022,905 B1 | 4/2006 | Hinman et al. |
| 7,505,989 B2 | 3/2009 | Gardner et al. |
| 7,865,534 B2 | 1/2011 | Chandra et al. |
| 8,489,334 B2 | 7/2013 | Chen et al. |

(Continued)

FOREIGN PATENT DOCUMENTS

| | | |
|---|---|---|
| EP | 1158447 A1 | 11/2001 |
| GB | 2350712 | 12/2000 |

(Continued)

OTHER PUBLICATIONS

Kankar et al.Proceedings of the 2002 SIAM International Conference on Data Mining Siam Publications (2002): pp. 548-565.*

(Continued)

Primary Examiner — Lori A. Clow

(74) Attorney, Agent, or Firm — Sterne, Kessler, Goldstein & Fox, P.L.L.C.

(57) ABSTRACT

Methods for identifying disease-related pathways that can used to identify drug discovery targets, to identify new uses for known drugs, to identify markers for drug response, and related purposes.

20 Claims, 5 Drawing Sheets

(56) References Cited

U.S. PATENT DOCUMENTS

| | | | |
|---|---|---|---|
| 8,793,073 B2 | 7/2014 | Chen et al. | |
| 2001/0049671 A1 | 12/2001 | Joerg | |
| 2002/0087275 A1* | 7/2002 | Kim | G06F 19/26 |
| | | | 702/19 |
| 2002/0165737 A1 | 11/2002 | Mahran | |
| 2002/0183936 A1* | 12/2002 | Kulp | G06F 19/28 |
| | | | 702/19 |
| 2002/0194201 A1 | 12/2002 | Wilbanks et al. | |
| 2003/0018522 A1 | 1/2003 | Denimarck et al. | |
| 2003/0171876 A1 | 9/2003 | Markowitz et al. | |
| 2004/0220969 A1 | 11/2004 | Cho et al. | |
| 2004/0236740 A1 | 11/2004 | Cho et al. | |
| 2004/0249620 A1 | 12/2004 | Chandra et al. | |
| 2005/0044071 A1 | 2/2005 | Cho et al. | |
| 2005/0055347 A9 | 3/2005 | Cho et al. | |
| 2006/0036368 A1 | 2/2006 | Chen et al. | |
| 2006/0064037 A1 | 3/2006 | Shalon et al. | |
| 2006/0143082 A1 | 6/2006 | Ebert | |
| 2007/0168135 A1 | 7/2007 | Agarwal et al. | |
| 2007/0282632 A1 | 12/2007 | Sachs | |
| 2008/0033819 A1 | 2/2008 | Leschly | |
| 2008/0255877 A1 | 10/2008 | Fernandez | |
| 2009/0183268 A1 | 7/2009 | Kingsmore | |
| 2010/0010957 A1 | 1/2010 | Cho et al. | |
| 2011/0098193 A1 | 4/2011 | Kingsmore et al. | |
| 2011/0191286 A1 | 8/2011 | Cho et al. | |
| 2014/0019404 A1 | 1/2014 | Cho et al. | |
| 2015/0024951 A1 | 1/2015 | Chen et al. | |

FOREIGN PATENT DOCUMENTS

| | | |
|---|---|---|
| JP | 11-259498 | 9/1999 |
| JP | 2001-134600 | 5/2001 |
| WO | WO 01/55911 A1 | 8/2001 |
| WO | WO 2002/099725 | 12/2002 |

OTHER PUBLICATIONS

"Online tests give instant feedback on office skills," NewsWire Association, 1998; 2 pages.
Aronow, B., "GeneSpring and GetNet," Briefings in Bioinformatics, vol. 2, No. 4, 2001; pp. 397-401.
Ashburner, M., et al., "Gene ontology: tool for the unification of biology,"Nature Genetics, vol. 25, No. 1, 2000; pp. 25-29.
Blaschke, C., et al., "Automatic extraction of biological information from scientific text: protein-protein interactions," ISMB, vol. 7, 1999; 8 pages.
Bura, E., et al., "The binary regression quantile plot: assessing the importance of predictors in binary regression visually," Biometrical Journal, vol. 43, No. 1, 2001; pp. 5-21.
BusinessWeek. "GM finally has a real winner,but success is bringing a fresh batch of problems," McGraw-Hill Co. Inc. Aug. 17, 1992; 6 pages.
Chakkour, F., et al., "Sentence analysis by case-based reasoning," Engineering of Intelligent Systems, 2001; pp. 546-551.
Chaudhri, V.K., et al., "OKBC: A programmatic foundation for knowledge base interoperability," AAAI/IAAI, 1998; 8 pages.
Chu, L., "GeneSpring TM: tools for analyzing microarray expression data," Genome Informatics, vol. 12, 2001; pp. 227-229.
Farquhar, A., "The ontolingua server: A tool for collaborative ontology construction," International Journal of Human-Computer Studies. vol. 46, No. 6, 1997; pp. 707-727.
Fujubuchi, W., "Gene & genome encyclopedia," Gene & Medicine, vol. 1, No. 2, 1997; pp. 119-124.
Goble, C., et al., "Transparent access to multiple bioinformatics information sources," IBM Systems Journal, vol. 40, No. 2, 2001; pp. 532-551.
Hafner, C., et al., "Ontological foundations for biology knowledge models," ISMB-96 Proceedings, 1996; pp. 78-87.
Halpin, T., "Object-role modeling (ORM/NIAM)," Handbook on Architectures of Information Systems, 2006; pp. 81-103.

Helden, J. V., et al., "Representing and analysing molecular and cellular function using the computer," Biological Chemistry, vol. 381, No. 9-10, 2000; pp. 921-935.
Hirota, et al., "Evaluation of ontology-driven information extraction," Proceedings of the Sixth Annual Meeting of the Assocation for Natural Language Processing, 2000; pp. 137-138.
Hughes, T. R., et al., "Functional discovery via a compendium of expression profiles," Cell, vol. 102, No. 1, 2000; pp. 109-126.
Inoue, A., "GenomeNet as a medical information resource." Gene & Medicine, vol. 4, No. 3, 2000; pp. 16-23.
Int. Search Report and Written Opinion dated Apr. 9, 2013 for App No. PCT/US2012/063753; 24 pages.
Int. Search Report dated Aug. 27, 2008, for App. No. PCT/US2007/746663; 2 pages.
Int. Search Report dated Jan. 10. 2003, for App. No. PCT/US02/35.650; 1 page.
Int. Search Report dated Jul. 22, 2004, for App. No. PCT/US03/03006; 8 pages.
Karp, P., et al., "HinCyc: a knowledge base of the complete genome and metabolic pathways of H. influenzae," ISMB, vol. 4, 1996; pp. 1-15.
Karp, P., et al., "Integrated pathway-genome databases and their role in drug discovery," Trends in Biotechnology, vol. 17. No. 7, 1999; pp. 275-281.
Katayama, T.,"Modeling of intermolecular interaction network, simulation, " Japan Technical Information Services Corporation (JATIS), vol. 20, No. 2, 2001; pp. 12-15.
Leach, R., Object-Oriented Design and Programming With C++, 1995; 13 pages.
Meltzer, P. S., "Spotting the target: microarrays for disease gene discovery," Current Opinion in Genetics & Development, vol. 11, No. 3, 2001; pp. 258-263.
Noy, N., et al., "The knowledge model of Protege-2000: Combining interoperability and flexibility," Knowledge Engineering and Knowledge Management Methods, Models, and Tools, 2000; pp. 17-32.
Office Action dated Jun. 10, 2009 for U.S. Appl. No, 10/632,099; 11 pages.
Office Action dated Dec. 30, 2010 for U.S. Appl. No. 10/632,099; 13 pages.
Office Action dated Feb. 2, 2011 for U.S. Appl. No. 11/829,784; 7 pages.
Office Action dated Jan. 13, 2010 for U.S. Appl. No. 10/502,420; 12 pages.
Office Action dated Jul. 1, 2011 for U.S. Appl. No. 10/502,420; 13 pages.
Office Action dated Jul. 2, 2010 for U.S. Appl. No. 10/632,099; 12 pages.
Office Action dated Jun. 16, 2010 for U.S. Appl. No. 11/829,784; 8 pages.
Office Action dated Jun. 9, 2009 for U.S. Appl. No. 11/829,784; 10 pages.
Office Action dated Mar. 14, 2012 for U.S. Appl. No. 12/499,761; 23 pages.
Office Action dated May 20, 2009 for U.S. Appl. No, 10/502,420; 16 pages.
Office Action dated Nov. 14, 2011 for U.S. Appl. No. 10/632,099; 15 pages.
Office Action dated Nov. 19, 2007 for U.S. Appl. No. 10/632,099; 11 pages.
Office Action dated Sep. 18, 2008 for U.S. Appl. No. 10/632,099; 16 pages.
Office Action dated Sep. 4, 2008 for U.S. Appl. No. 11/829,784; 11 pages.
Office Action dated Sep. 8, 2010 for U.S. Appl. No. 10/502,420; 12 pages.
Oliver, D., et al., "Ontology development for a pharmacogenetics knowledge base," Pacific Symposium on Biocomputing, vol. 7, 2002; 14 pages.
Qu, K., et al., "Multidimensional data integration and relationship inference," IEEE Intelligent Systems, vol. 2, 2002; pp. 21-27.
Rindflesch, T.C., et al., "Extracting molecular binding relationships from biomedical text," Proceedings of the Sixth Conference on Applied Natural Language Processing, 2000; 8 pages.

(56) References Cited

OTHER PUBLICATIONS

Rzhetsky, A., "A knowledge model for analysis and simulation of regulatory networks," Bioinformatics, vol. 16, No. 12, 2000; pp. 1120-1128.

Sekimizu, T., et al., "Identifying the interaction between genes and gene products based on frequently seen verbs in medline abstracts," Genome Informatics, vol. 9, 1998; pp. 62-71.

Supplementary European Search Report dated Sep. 21, 2007, directed to App. No. 02778752.2; 3 pages.

Thomas, J., et al., "Automatic extraction of protein interactions from scientific abstracts," Pacific Symposium on Biocomputing, vol. 5, 2000; 12 pages.

Yokohama, T., "An object-oriented and constraint-based knowledge representation system for design object modeling," Sixth Conference on Artificial Intelligence Applications, IEEE, 1990; 7 pages.

Office Action dated Aug. 1, 2013 for U.S. Appl. No. 11/829,784; 8 pages.

Office Action dated Apr. 22, 2014 for U.S. Appl. No. 11/829,784; 8 pages.

Office Action dated Aug. 29, 2013 for U.S. Appl. No. 10/632,099; 14 pages.

Notice of Allowance dated Mar. 14, 2014 for U.S. Appl. No. 10/632,099; 7 pages.

Notice of Allowance dated Jun. 3, 2013 for U.S. Appl. No. 10/502,420; 8 pages.

Office Action and Search Report directed to related Canadian Application No. 2,474,754 dated Jun. 11, 2015; 6 pages.

Nebel, B., "Frame-based systems," MIT Encyclopedia of the Cognitive Sciences, 1999; pp. 324-325.

Rzhetsky, A., et al., "A knowledge model for analysis and simulation of regulatory networks in bioinformatics studied aiming at disease gene discovery," AMIA 99 Fall Annual Symposium; pp. 1-5. 1999.

* cited by examiner

DRUG DISCOVERY METHODS

This application is a continuation of U.S. Pat. No. 10,502,420, filed Aug. 26, 2005, which is a National Stage Application of PCT/US03/03006 filed on Feb. 3, 2003, which claims the benefit of U.S. Provisional Application No. 60/421,772 filed Oct. 29, 2002 and U.S. Provisional Application No. 60/353,176, filed Feb. 4, 2002, all of which are incorporated herein by reference.

FIELD OF INVENTION

This invention relates to methods of drug discovery and, in particular, utilizing an information database relating to genomics data for the purposes of understanding phenotypic traits.

BACKGROUND OF THE INVENTION

The last 5 years or so has seen an explosion in the availability of data relating to genomics, i.e., information related to genes, their nucleic acid sequences, the proteins these genes encode for, the biological effect of the proteins, and other related information. The availability of this data has opened up unprecedented opportunities for understanding disease pathways and for identifying new therapies and prophylaxes based on these understandings.

There are multiple routes to modern drug discovery. In general, these require identification of a gene or gene product (i.e., an RNA, polypeptide or protein) that is associated with a given disease. After this association has been made, researchers can design drugs that antagonize or inhibit, or agonize or enhance, the expression of or activity (i.e., function) of the gene or gene product in order to treat or prevent the disease.

Preferably, researchers will have not only knowledge of the association of a given gene or gene product with a disease but a fuller understanding of the entire disease pathway, i.e., the series of biochemical processes within the body that result in disease. Researchers also desire to have a fuller understanding of other pathways that may comprise the given gene or gene product, as well as other pathways, i.e., pathways that do not comprise the gene or gene product, that lead to the same disease. Even more preferably, researchers would wish to have a fuller understanding of additional indicators of safety and efficacy, such as genotypic or phenotypic "markers" or biochemical or environmental factors that are associated with responses to specific drugs, which responses vary among subsets of a patient population.

So, for example, the knowledge that a hypothetical protein, referred to now for illustrative purposes as Protein A, is associated with inflammation suggests to researchers that Protein A is a likely target for drug intervention because a drug that inhibits Protein A is likely to have a positive effect on Protein A-related inflammation.

Researchers would prefer to have a fuller understanding of the association of Protein A to inflammation. For illustrative purposes, researchers would want to know, hypothetically:

Up regulation of Gene A results in expression of Protein A

Protein A phosphorylates Protein B certain cell types

Protein B, upon phosphorylation, up regulates Gene C

Up regulation of Gene C results in expression of Protein C

Protein C activates T cells

Activation of T cells causes inflammation.

More preferably, the researchers would also have a fuller understanding of additional pathways that may comprise Protein A, as such information would help researchers predict side effects. Also, researchers would wish to have a fuller understanding of alternative pathways that result in the same disease because such information would help them better predict the efficacy of inhibiting Protein A. As noted above, researchers would also want to understand more fully additional factors that would help them predict safety or efficacy in given patients. Genotypic markers typically comprise specific polymorphisms, such as repeats, SNPs, insertions or deletions; phenotypic markers can include a number of factors such as race, gender, ethnicity, age, weight, etc.; environmental factors can include, e.g., behaviors such as smoking or drinking alcohol, exposure to toxins, etc.; biochemical markers can include, e.g., cholesterol levels, etc.

A great deal of such information is available from public sources, e.g., scientific publications. However, the sheer volume of such data is overwhelming such that the data cannot be accessed and correlated in an efficient and effective manner. Compounding the problem is that the data are in disparate sources making it extremely hard to piece together in order to derive a fuller picture.

There have been several attempts to address this problem by creating search tools, such as MedLine, Chemical Abstracts, Biosis Previews, etc., that permit computer searching of large numbers of scientific journals or abstracts, such as Science, Nature, Proceedings of the National Academy of Sciences, etc. Searching these journals is still a problem because there are hundreds of such journals and many can only be searched by key words (and searching is sometimes restricted to key word fields or abstracts) or by reading full abstracts, which in either case is very time-consuming and inefficient such that important articles are easily missed.

Another partial solution is databases of genomics data. One example is GenBank, which is maintained by NCBI. Gene sequences entered in such databases are usually annotated with information that may include, e.g., the type of cell in which a given gene sequence is expressed, the probable function of the sequence, etc.

While these databases are enormously helpful, they miss some data that appear in scientific publications and, more problematically, they cannot readily be used to determine disease pathways because the data are not structured in a way that allows computer analysis of complex relations between different genes and gene products.

SUMMARY OF THE INVENTION

The present invention relates to methods for identifying pathways for particular phenotypic traits. In a particular representative embodiment, the invention relates to methods of identifying drug discovery targets by defining disease pathways by computer analysis of direct as well as complex relations among different genes, gene products, or processes. In other embodiments, the invention provides methods for identifying new uses for known drugs, methods for predicting likely side effects of treatment with a given drug, and methods of predicting efficacy of a given drug in a given individual.

The invention makes use of a structured database representation of information concerning genes, gene products, processes, and phenotypic traits of interest, and optionally other information (including for example information concerning SNPs, non-genomic DNA sequences, allelic variations, etc.) such that relationships that are several steps removed and that may be multi-directional, can be identified. The information that is stored typically comprises data from public sources such as databases and scientific publications. It can also be proprietary data or a mix of proprietary and public data. The phenotypic trait of interest is typically a disease, a susceptibility to a disease, or a drug response, e.g., a side effect or a degree of efficacy.

A structured database representation of information will be able to define biological relationships that are at least one step removed. For example, information that may be acquired from one data source, e.g., a scientific journal article, might conclude that Protein A phosphorylates Protein B. Information from a second data source, e.g., a second scientific journal article, might conclude that Protein B, upon phosphorylation, up regulates Gene C. The relationship between Protein A and Gene C is one step removed. Each such "step" can actually involve a number of biological interactions between or otherwise affecting the relationship between or among two or more components of the body. Preferably, the system will be able to define biological relationships that are 2, 3, 4, 5, 6, 7, 8, 9, or 10 or more steps removed. The biological relationships that can be defined will often times be complex, or multi-directional, relationships in the sense that one or more genes or gene products in a given pathway may also appear to be parts of multiple other pathways so that many of the genes or gene products in the database will be related to others in a complex, "spiderweb-like" relationship. A biological relationship exists when a component (i.e., concept) of a pathway has a biological effect upon, or is biologically affected by, another component of the pathway. So, with reference to the simple illustration provided above, a biological relationship exists between any two of, and among all of, Protein A, the gene that expresses protein A, Protein B, the gene that expresses Protein B, Gene C, and the gene product of Gene C. Thus, a preferred database for use in the invention may be referred to as a "biological relationships database," i.e., one that identifies related biological concepts and that specifies what the functional biological relationship (or functional biological relationships) between or among the concepts is (or are).

There are several uses for a structured database representation of genomics information. In one such use, a method for identifying a drug discovery target includes the steps of querying the database to identify a disease-related pathway whereby each of the "actor concepts" in the pathway (as described hereinbelow) is an actual or putative candidate drug discovery target. The genomics information may comprise information relating to the biological interactions of each of the "concepts" in the pathway, both within the pathway as well as external to the pathway. Such external information can be used to select, de-select, or prioritize certain "steps" as drug discovery targets.

The candidate drug discovery targets in the disease related pathway may be prioritized based on factors that include function and complexity, a presence of markers for side effects and patient responsiveness, and "drugability" (this term is used in the field of drug discovery to indicate the likelihood that the activity of a particular biological entity can be affected by use of a pharmaceutical agent, e.g., by looking at the protein family class (e.g. GPCR family members generally considered more easily target-able because they sit on the cell surface), through structural analysis, or other experiences. Results of querying the database may be combined with the results of additional data obtained from one or more additional methods for identifying candidate drug discovery targets (e.g., differential gene expression studies).

The database may include the use of an "ontology" as this particular form of structured information may be used to infer classifications based upon the biological interactions of interest. This classifying one or more findings using an ontology may further include determining a likelihood that the one or more findings residing in a particular biological classification in the ontology is statistically significant (e.g., by testing a null hypothesis).

In another aspect, there is a method for identifying a new use for a known therapy including the steps of providing a means for querying the database to identify a disease-related pathway comprising a known therapy target; selecting at least one of such disease-related pathways wherein the known therapy target is also comprised within a second disease-related pathway; and identifying treatment of the second disease as a new use for the known therapy.

In another aspect, a method for prioritizing candidate development compounds for further development is provided. In this embodiment, the method includes the steps of querying the database to identify all pathways associated with the target of each candidate development compound and giving higher priority to development compounds on the basis of whether or not they are likely to result in an undesirable effect based on their involvement in other biological pathways.

In another aspect, a method for identifying disease-related pathways wherein the disease is a side effect of drug therapy is provided. In this embodiment, the method includes the steps of identifying the disease-related pathway affected by a drug or drug discovery target and providing a means for querying the database to identify alternative pathways that are also affected by the drug or the drug discovery target and that result in the undesirable phenotype.

In another aspect of the invention, a method for identifying or validating a genotypic marker for a disease state includes providing a means for querying the database to identify a genotypic marker that is associated with a disease state.

In another aspect of the invention, a method for evaluating user-supplied genomics data is provided. In this embodiment, the steps include (a) defining a profile model based on one or more profile definition criterion; (b) building a collection of profiles according to the profile model; (c) identifying one or more profiles that overlap at least a portion of the user-supplied genomics data and determining, for each such overlapped profile, whether the overlap is statistically significant; and (d) analyzing one or more statistically significant profiles together with the user-supplied genomics data including inspecting database-asserted biological interactions embodied in the one or more statistically significant profiles. The building step may further include building profile libraries containing a plurality of profiles, each one of which being based upon a unique profile model. The profiles may correspond to static profile models, i.e., pre-generated, or dynamic, i.e., created on an as-needed basis by direct queries of the database. In the former case, a separately stored, structured representation of profiles is the primary focus for subsequent analysis, rather than the database or a copy of the database.

Profiles may be generated using one of a data-driven and model-driven approach and each of the profiles may be generated by building a profile about a central genomic data type, e.g., gene, gene product, process. Statistical significance may be measured in other ways, such as the statistical significance of one or more biological associations that appear to correlate with the overlapped profiles.

A fuller description of these embodiments of the invention, as well as other embodiments of the invention, which will become apparent from the following detailed description, follows. It is to be understood that both the foregoing general description and the following detailed description are exemplary and explanatory and are intended to provide further explanation without limiting the scope of the invention as claimed.

BRIEF DESCRIPTION OF THE FIGURES

The accompanying drawings, which are included to provide a further understanding of the invention, are incorporated in and constitute a part of this specification, illustrate preferred embodiments of the invention and together with the description serve to explain the principles of the invention. In the drawings.

DETAILED DESCRIPTION

Definitions

Figure 1:
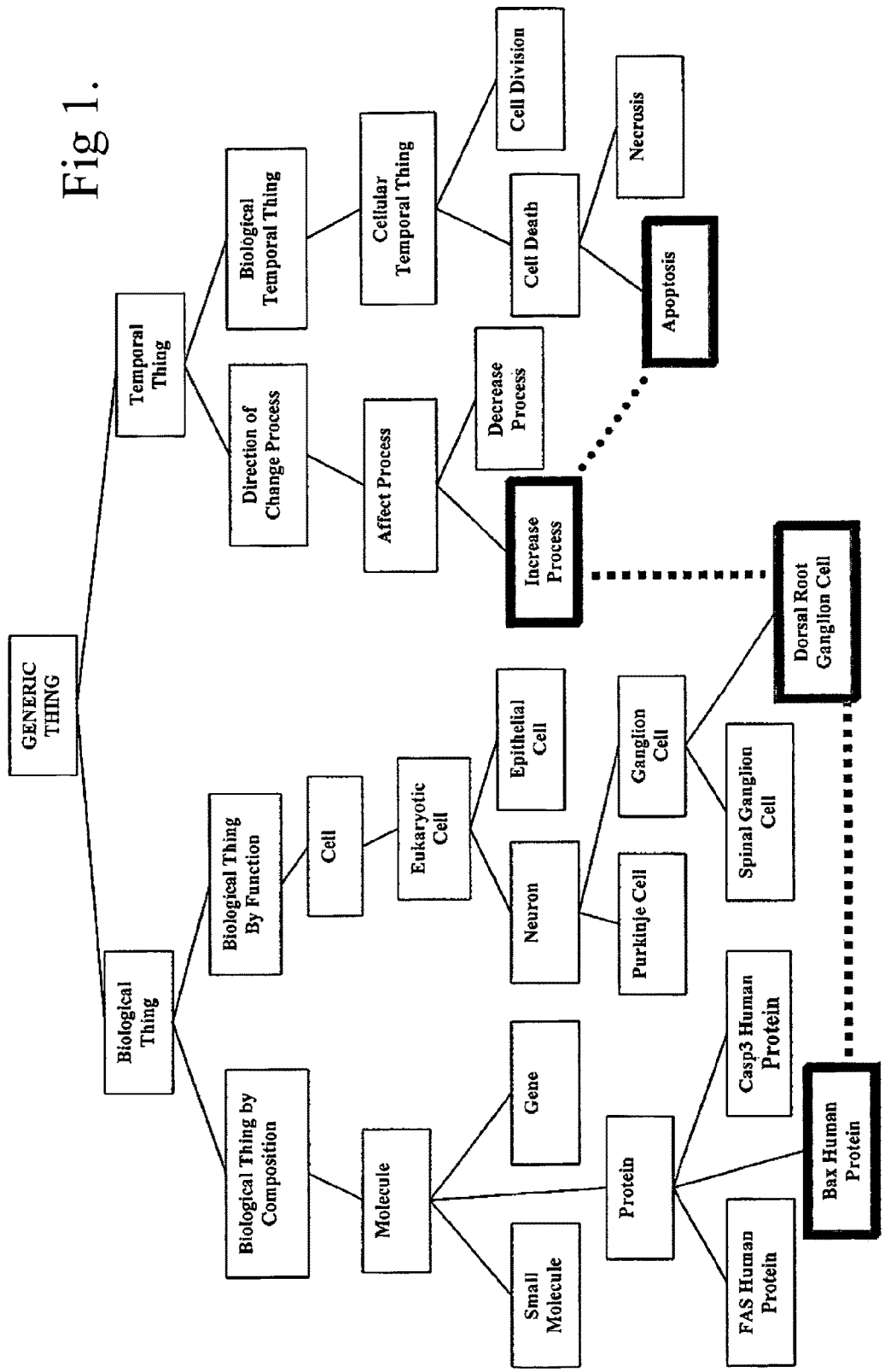
FIG. 1 illustrates the positioning within an ontology of the finding, "Human Bax protein accelerated the death by apoptosis of rat DRG neurons after infection with Sindbis Virus."

As used in the description that follows:

"Disease" means any phenotype or phenotypic trait of concern, including by way of example a disease or disease state, a predisposition or susceptibility to a disease, or an abnormal drug response. Illustrative and non-limiting examples of disease states include high cholesterol levels, congestive heart failure, hypertension, diabetes, glucose intolerance, depression, anxiety, infectious disease, toxic states, drug therapy side effects, inefficacy of drug therapy, alcoholism, addiction, etc.

A "disease-related pathway" is a series of biochemical reactions in the body that result in disease, i.e., it is a series, linear or branched, of biological interactions in the body that collectively have an effect on a disease state, e.g., initiation, progression, remission, or exacerbation. Such biological interactions, i.e., biological effects or functional relationships, are the biological processes that occur within the body, e.g., binding, agonizing, antagonizing, inhibiting, activating, modulating, modifying, etc.

"Therapy" and "therapeutic" include prophylaxis and prophylactic and encompass prevention as well as amelioration of symptoms associated with a disease state, inhibition or delay of progression of a disease state and treatment of a disease state.

"Protein" or "gene product" means a peptide, oligopeptide, polypeptide or protein, as translated or as may be modified subsequent to translation. A gene product can also be an RNA molecule.

"Findings" are the data that is used to build an information database. This data may come from public sources, such as databases and scientific publications, but it may also include proprietary data or a mix of proprietary and public data. In preferred embodiments, findings are derived from natural language (e.g., English language) formalized textual content according to methods outlined in greater detail below.

"Biological effect" includes the molecular effects of a given biological concept as well as the effects of such concept at the level of a cell, tissue or organism.

Unless otherwise specified, "include" and "includes" mean including but not limited to and "a" means one or more.

The Database

In a preferred embodiment, information is stored in, and accessed using two databases. The first database is a knowledge base ("KB") of the scientific findings structured according to predetermined, causal relationships that generally take the form of effector gene (and/or product)→object gene (and/or product) type relationships (hereinafter the "Findings KB"). The preferred database structure for this Findings KB is a frame-based knowledge representation data model, although other database structures may alternatively be used for structuring the scientific findings. The second database type is an ontology. An ontology is a multiple-hierarchical representation of the taxonomy and formal concepts and relationships relevant to the domain of interest, preferably organized in a frame-based format. The Findings KB and ontology are herein collectively referred to as a knowledge representation system ("KRS"). Other database structures, comprising one or more knowledge bases comprising a KRS, may be employed for representing a body of knowledge when practicing the invention. However, when an ontology is used together with other KBs to form a KRS, or solely as a KRS, the methods of the invention can leverage the taxonomy and formal concepts and relationships defined in an ontology for purposes of inferring conclusions about scientific findings which may not otherwise be readily apparent, especially where findings form part of a complex, or multi-directional series of causal events. Accordingly, provided below is a further description of a preferred ontology that may be used to practice the invention.

With respect to the preferred embodiments, the principal domain of interest is genomic information, which comprises at a minimum information relating to genes, their DNA sequences, mRNA, the proteins that result when the genes are expressed, and one or more biological effects of the expressed proteins but which can include other, related information. It will be clear to the reader that the genomics information can also be information relating to other genomics, proteinomics, metabolic and behavioral information, as well to other biological processes and to biological components other than proteins and genes, such as cells, including, e.g., the biological effects of cells. A preferred ontology structure stores its contents in a frame-based format, which allows searching of the ontology to find relationships between or to make inferences about items stored in the ontology. In this illustrative ontology, the primary organizational grouping is called a class. A class represents a group of things that share similar properties. For example, in the ontology described herein, one class is human cells, which class includes lung cells, skin cells, brains cell and so on.

Each of the members of a class is an "instance" of that class, which instances represent single items or elements belonging within the specified class. Thus, an individual blood cell is an instance of the class of human cells.

The relationships between different instances in the ontology are defined by "slots." Slots can be thought of as the verbs that relate two classes. For example, pancreatic Beta cells have a slot, "produce," linking them to insulin. A "facet" represents more detailed information about a "slot" and can in some cases restrict the values that a slot can have when related to specific instances of a class. The slots and facets define and structure the taxonomic relationships and partonomic relationships between classes. When scientific findings are entered into the ontology, each finding is separated into its discrete components, or "concepts." So, for example, in the finding: "Human Bax protein accelerated the death by apoptosis of rat dorsal root ganglion ("DRG") neurons after infection with Sindbis Virus," each of the following bracketed phrases is a concept: [Human Bax protein] [accelerated] the [death] by [apoptosis] of [rat] [DRG neurons] after [infection] with [Sindbis Virus]. The actor concepts are the physical biological components of the pathway that cause or lead to another reaction in the pathway. In the instant example, the actor concepts are Human Bax protein and Sindbis Virus. Actor concepts, each of which is a putative drug discovery target, are likely to be genes or gene products (including, e.g., receptors and enzymes) but can also be, e.g., other DNA sequences (including, e.g., DNA that is not transcribed or that is not transcribed and translated) RNA (including, e.g., mRNA transcripts) cells, and bacteria, viruses or other pathogens.

FIG. 1 illustrates how these concepts are structured in a preferred ontology. As illustrated, Human Bax protein is a subclass of protein; apoptosis is a subclass of death, and DRG is a subclass of neuron. This figure also illustrates how the concepts in this simple, illustrative finding are related to each other, making it easier to visualize how each of these concepts can be further linked to other concepts in other findings, at the same level and at higher and lower levels. In a preferred embodiment of the invention, findings are structured to represent causality, thus permitting the discovery of unidirectional sets of findings that are likely to lead, collectively, to a given biological effect.

Clearly, for the ontology to be effective, it is preferable to develop a common set of terms for like things. It is a well-recognized problem in fast moving scientific fields, like genomics, for different terms to be applied by different laboratories to the same genes, proteins or other biological materials, and for terminologies to change over time as conventions develop. Thus, the storing and accessing of genomics information will preferably be organized to ensure semantic consistency. For example, data entry could be limited to a pre-set, or glossary of terms, inclusion of a scientific thesaurus that automatically converts inputted terms into accepted terms, and human review to update the thesaurus or glossary.

Regardless of the subject matter captured and described by the ontology, whether genomics or toxicology, it is necessary to examine closely the body of knowledge that comprises the subject matter so that the knowledge can be organized into the proper classes and linked by the appropriate slots and facets and finally stored in a form that will allow the contents and the relationships contained in the ontology to be properly represented, searched, accessed and maintained.

The selection of sources for the information or "facts" that will be included in the ontology and the methods used to digest those sources so that the facts can be supplied to the ontology in proper form are described in commonly-assigned patent applications: (1) Ser. No. 09/733,495, filed on 8 Dec. 2000 and entitled, "Techniques for Facilitating Information Acquisition and Storage;" and (2) Ser. No. 10/038,197, filed on 9 Nov. 2001, entitled "Method and System for Performing Information Extraction and Quality Control for a Knowledge base, the contents of all of which are incorporated by reference herein for all purposes.

As described more fully in those references and below, scientists who read the articles that comprise a data source for the ontology may abstract the facts contained in those articles by filling in fact templates. An abstracted fact refers to a fact retrieved from an information source that is rewritten (e.g., by using a template) in the computational information language of the ontology. A completed fact template is called an instantiated template. The contents of the instantiated templates are placed in the ontology. The type and format of these fact templates are dictated by the content and structure of the ontology. The information contained in these facts are also stored in the Findings KB, which, as mentioned above, is used to store scientific findings. Although all information in the Findings KB is also contained in the ontology, it is preferred to use the Findings KB when specific findings are later retrieved as this can facilitate computational efficiency for searches of multiple findings where information about the classification of, e.g., the effector and/or object in the finding within the ontology is not needed.

Each type of permitted fact of the ontology can also be associated with a fact template that is created to facilitate the proper entry of the information or data comprising that particular type of fact into the ontology. These fact templates are presented to scientists as they abstract information from the sources. Pull-down menus within the template present the scientist with the appropriate classes, slots and facets for the particular fact type.

The process of abstracting information is called structuring knowledge, as it places knowledge into the structure and architecture of the ontology. The method for structuring the knowledge is based on formalized models of experimental design and biological concepts. These models provide the framework for capturing a considerable portion of the loosely articulated findings typically found in academic literature. The specific level of experimental results that is of greatest value to industrial and academic scientists can be particularly targeted for capture. So, for example, in the field of genomics, knowledge that focuses on the effects that both perturbation to genes, gene products (RNA and proteins) and small molecules and various physical stimuli have upon biological systems is singled out. These perturbations and stimuli form the backbone of the ontology and provide the necessary framework for developing a more sophisticated representation of complex biological information.

Examples of the types of facts and biological relationships that can be translated into the ontology are: a) an increase in the amount of Fadd protein increases apoptosis; b) a decrease in Raf levels increases activation of Rip2; and c) the allele delta32 of CCR5, compared to the wild-type allele, decreases HIV transmission. In a preferred embodiment, biological systems are defined in terms of processes and objects. Discrete objects are physical things such as specific genes, proteins, cells and organisms. Processes are actions that act on those objects. Examples of processes include phosphorylation, which acts on discrete objects such as proteins, and apoptosis, which acts on cells. Perturbation of an object can have an effect on a process or on an object.

Using these concepts of objects and processes, the information in the ontology may be represented by a variety of fact types.

As mentioned above, templates are associated with each fact type. In a preferred embodiment, there are five template types used for fact entry into the ontology. The corresponding fact types may be described as observational facts, comparison facts, case control facts, case control modifier facts, or case-control comparison facts. Of course, the structure and variety of fact types depend on the field of knowledge of the ontology, all of which will be known to those skilled in the art.

Examples of each of the aforementioned fact types of a preferred embodiment follow. Observational facts (OFs) are observations about something. An example of an OF is "Tyrosine phosphorylation of INRS-1 was observed." Comparison facts (CFs) compare a property of one thing to a property of another thing. An example of a CF is "The size of a lymphocyte in one organism is greater than the size of a lymphocyte in another organism." Case control facts (CCFs) describe an alteration in something which causes changes to a property aspect of something. An example of a CCF is "Mouse-derived Brca-1 increased the rate of apoptosis of 293 cells." Case control comparison facts (CCCFs) compare the effect that something has in a first fact to the effect that something has in a second fact. An example of a CCCF is "Fas increases total apoptosis of 293 cells with Brd4 (introduced by vector transformation) more than it increases total apoptosis of 293 cells without Brd4." Case control modifier facts (CCPMFs) express an alteration in something that causes changes to a property of a modifier of a process. An example of a CCPMF is "Mouse-derived BRCA-1 increased the rate of the induction of 293 cell apoptosis."

Despite the restraints imposed by a template pull-down menu system and the template's isomorphic relationship with the ontology structure for each of the above fact types, there may still exist an enormous number of permutations of values for each type. The consequences of an incorrectly instantiated template are potentially serious, as erroneous entries in the ontology would necessitate a quality control process to address the incorrectly entered fact. This process can be expensive and time-consuming. Moreover, for those who are relatively inexperienced in the field of knowledge engineering, it is not always an easy task to recognize subtle differences between a correct and incorrect fact abstraction when facts are represented in the structured language of the ontology. This is especially true when an instantiated template represents a complex fact. To meet this need, natural language fact verification by a scientist may be included as part of knowledge acquisition. In a preferred embodiment, a fact verification scheme includes a natural language display of the fact derived from the template so that a scientist can verify, by reviewing the natural language representation of the structured fact entered into the template, whether the fact entered into the template was the fact as intended.

Alternatively, or additionally, information is extracted automatically by use of a computer to "read" and analyze papers and to extract data therefrom for inclusion in the ontology. In these embodiments, a natural language (e.g., English) source text is first interpreted using computational linguistics to determine, to the extent possible, the precise meaning of the "fact" contained in the natural language source. After this "fact" has been determined, it may be reviewed and then abstracted according to an automated procedure, manual procedure (i.e., human involvement) or a combination of both. Preferably, a combination manual and automated procedure is used to verify that the fact extracted from the source text is both a fact of interest, that it accurately reflects the intended meaning of the source text, and that it is appropriately structured for storage in the ontology. The data sources are not restricted to journal articles. Other data sources include, e.g., public databases, private databases, and proprietary data such as confidential data developed within and confined to a particular laboratory.

With data from multiple sources acquired and stored in the database, such as is described above, it is possible to determine relationships among genes and gene products that previously would have been exceedingly difficult or even impossible to identify because, e.g., of the number of sources from which data are required and the use of inconsistent language (e.g., different names for the same protein are used simultaneously or over time.) So, while it may be possible for one or a small number of individuals to stay abreast of all or most publications relating to a very narrowly defined field, it is impractical to think of scouring public data sources to identify disease pathways that comprise drug discovery targets without the aid of a structured database, such as is described above. Even with respect to particular diseases, genes or gene products, this task can be enormously difficult and time-consuming without the aid of a structured database.

Findings information may come from informal sources, as well as the more formalized documents and publication sources discussed above. For example, findings may be extracted using a network search tool that searches a network and then attempts to extract information contained in pages that seem to be about a biological concept of interest (e.g., a web-crawler that searches over the internet). Alternately, or additionally, a search engine may be used to scan corporate email, discussion groups, PowerPoint presentations, etc., to try to identify and then extract information relating to biological functions. Of course, one should expect a lower quality of results from these sources, both because the data parsing would be automatic, there would likely be higher error rates than manually entered content, and the content sources will more likely be informal or invalidated discussions, rather than peer-reviewed journals and the like.

Findings need not be limited to literature-based private or public information. For example, findings could include findings derived from, e.g., a company's microarray chip experiments. In this case, the array data could be reviewed to try to identify which genes are being co-expressed and/or co-regulated, from which a "A<→B" relationship could be deduced. These findings could then go into the KB directly or into a graph structure directly. The data may also include findings that scientists enter directly, or could be data straight from experiments (i.e. w/out interpretation by scientists).

The findings acquisition process discussed above may also be useful as a tool for publication, in addition to a data extraction or entry process. Much in the way that authors need to include abstracts and indexing keywords when proposing a publication for submission, they might also be required to write down their key conclusions in "findings format". In this contemplated use, the author or a 3rd party may perform the findings extraction (e.g., as in the way the National Library of Medicine is currently responsible for approving, if not creating, the keywords associated with paper abstracts).

KRS technology is not required for creating a structured database. While KRS technology may be preferred as it can simplify certain tasks in the data acquisition and data structuring process, it is also possible to create a KB using existing relational, object or XML database technology.

Figure 2:
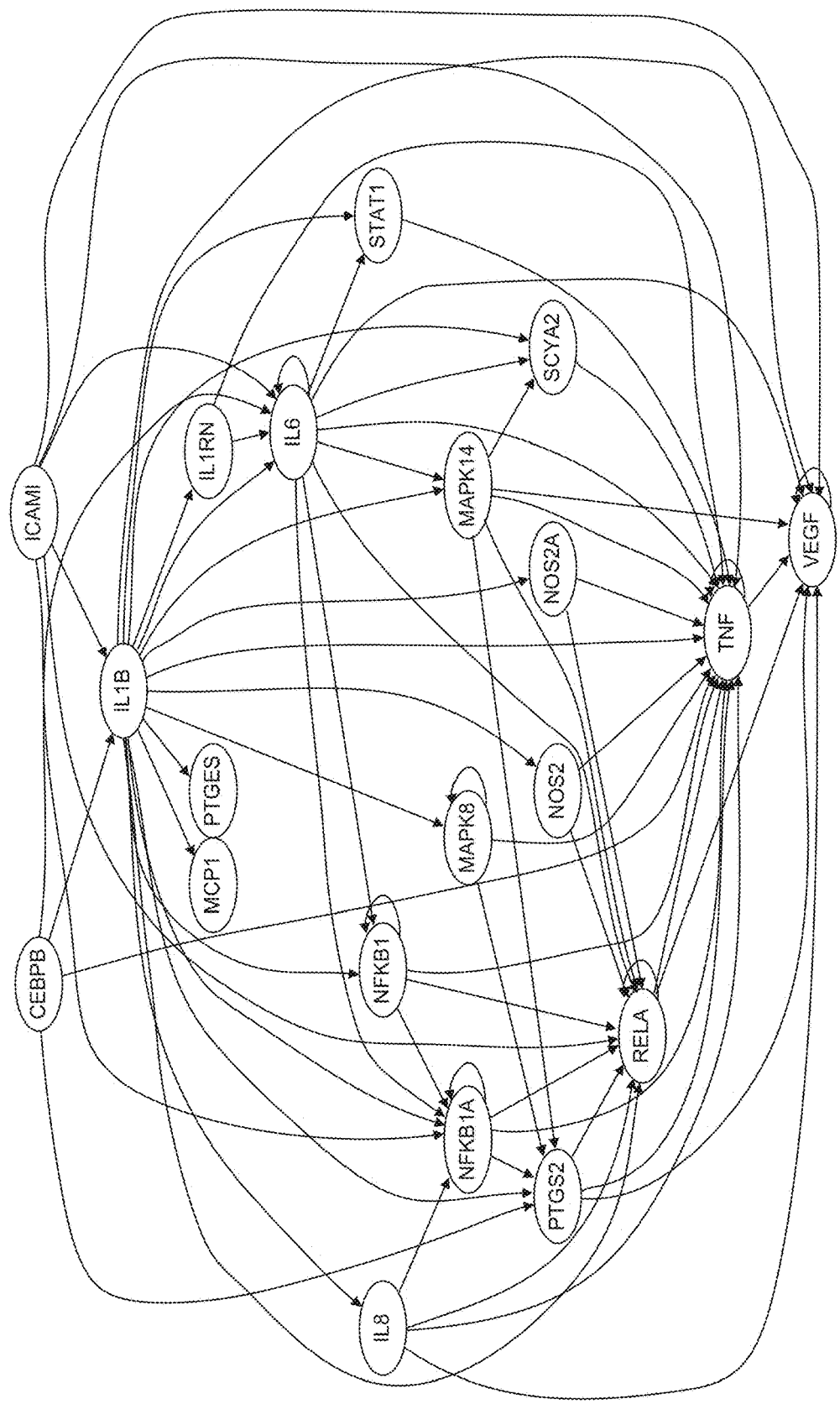
FIG. 2 illustrates a graphical example of the complex relationships among concepts involved in disease-related pathways.

With an ontology such as described above, it is practical to query the knowledge representation system for actor concepts, e.g., genes and gene products, related to a disease and thereby to construct a disease-related pathway that extends back several steps, and that branches out to identify overlapping disease-related pathways, as described above. Each gene or gene product in the pathway is a candidate drug discovery target because it is at least theoretically possible to treat the disease state by interrupting the disease-related pathway at any point. It will be clear to persons of skill in the art that further validation of such targets may be appropriate prior to incorporating such targets into a drug discovery program. Such further validation, if any, can be done in an number of ways including by correlating the targets with other relevant data, such as differential gene expression data as described below, or by use of animal models, including but not limited to transgenic knockouts. So, with respect to the findings illustrated in FIG. 1, human Bax protein is a candidate drug discovery target because inhibiting the expression of or activity of the protein will potentially avoid acceleration of apoptosis of DRG neurons after infection with Sindbis Virus. FIG. 2 illustrates slightly more complex relationships in disease-related pathways.

In general, the database is queried to identify pathways to a phenotypic trait, e.g., a disease state or a predisposition to a disease state or other phenotypic trait of interest, by constructing a query designed to produce a response, following computational analysis of the database (or ontology), that reveals all concepts that are biologically related to the phenotypic trait state or to a biological component of the body that is already known to be biologically related to the phenotypic trait. The query can also fix the number of steps removed from the phenotypic trait or other biological component. So, with reference to the simple illustration provided in FIG. 1, a query might be, e.g., "Identify all concepts that are related to apoptosis of DRG neurons."

The means for storing and accessing genomics information and the means for computational analysis of complex relationships among the stored concepts will typically comprise a computer system, i.e., any type of system that comprises stored, e.g., digitized, data and a means to query the stored data. Such computer system can be a stand alone computer, a multicomponent computer, e.g., one in which the stored data are physically remote from the user interface, networked computers, etc. Any known means for querying the database will also be useful, e.g., software and hardware for electronically searching fields, categories or whole databases.

Thus, in one aspect, the invention comprises a method for identifying a candidate drug discovery target by (a) providing a means for storing and accessing genomics information wherein said means permits computational analysis of complex relationships among the stored concepts; (b) querying the database to identify a disease-related pathway; and (c) identifying the biochemical reactions in the disease-related pathway whereby each of the actor concepts involved in each such reaction is a candidate drug discovery target.

In a preferred embodiment, the candidate drug discovery targets are prioritized based on their function and complexity. For example, gene products that phosphorylate or activate a second gene product may be of special interest, as may gene products that are "simple" in the sense that they are involved in few other pathways and therefore are less likely to produce undesirable physiological effects. On the other hand, "two-hybrid data" might be considered to have a lower likelihood of representing an actual functional or physiological effect because two-hybrid experiments measure only simple protein-protein interactions and therefore provide a relatively impoverished representation of biological function and state. In addition, two-hybrid experiments have a relatively high false positive rate, resulting in noisy data that might further reduce the likelihood of representing true biological function. Similarly, genes that have highly redundant links, i.e., are involved in multiple other pathways, may be deprioritized because as targets their disruption may be expected to disrupt a number of pathways. Similarly, pathways to disease for which there are multiple pathways are also, in general, less preferred.

More preferably, candidate drug targets are also prioritized based on involvement in other pathways that are unlikely to result in unwanted side effects. For example, inhibiting a gene product such that a desirable biochemical pathway is unintentionally inhibited is likely to result in unwanted side effects and should, in certain cases, be avoided. Thus, in an aspect of the invention, the means for storing and accessing the genomics information may be used to predict side effects or non-responsiveness by queries that identify all known pathways linked to a candidate drug discovery target, which would include pathways of genes and gene products that would be undesirably affected by affecting the candidate drug discovery target.

In cases in which there are multiple pathways to a disease, the invention may also be used to identify multiple drug discovery targets leading to development of an adjunctive therapy that may include administering more than one drug, whereby multiple pathways to the same disease are interrupted. In some cases, there may be an existing known drug for one or more of the alternative pathways.

In some cases, it is not clear how a drug undergoing pre-clinical or clinical development is effective in treating a disease because the association between the drug target and the disease is not well-understood. In one aspect of the invention, there is provided a method for determining or validating the mechanism of action of a drug which comprises using the means for storing and accessing genomics information to define the pathway or pathways between the drug target and the disease.

The invention can be used to aid target validation by elucidating other pathways that may be affected by agonism or antagonism of a candidate drug discovery target and by showing alternative pathways that might complement or replace the pathway affected by drug intervention at the point of a given candidate drug discovery target.

In another aspect, this invention comprises a method for identifying diagnostic markers for a given disease. In this aspect, the invention comprises: (a) providing a means for storing and accessing genomics information wherein said means permits computational analysis of complex relationships among the stored concepts and (b) querying the database to identify markers that are associated with the disease. The markers that are associated with the disease are typically genetic markers, i.e., polymorphisms such as repeats, inserts, deletions, SNP's, etc. They can also be protein markers, i.e., proteins that are expressed or not expressed, relatively under expressed or over expressed, post-translationally processed differently or mutated. Other markers are also useful, e.g., antibodies, mRNA, biochemical markers such as enzyme or metabolite levels, etc.

The present invention is also useful in the growing field of pharmacogenomics. For example, in another aspect, the invention provides a method for identifying diagnostic markers specifically for drug response, i.e., unwanted side effects or non-responsiveness. By identifying markers for side-effects or non-responsiveness, a population of patients having a given disease can be stratified into sub-populations based on likelihood of having a serious adverse event or for not responding to a given therapy, for purposes of enrollment in clinical trials or for treatment.

The invention in yet another aspect comprises a method for identifying new uses for known drugs. In this aspect, the invention comprises using the means for storing and accessing genomics information to identify all pathways in which the target of the known drug is involved, additional to the pathway for the disease for which the drug is indicated, and then determining which if any of the additional pathways result in a different disease. In this way, it is possible to identify different diseases, i.e., new uses, for the known drug.

The method of the invention for predicting disease pathways and targets for drug discovery may be enhanced by leveraging the information obtained by querying a database with data obtained from other methods for identifying disease pathways or targets for drug discovery. For example, the method of the invention may include, additionally, the use of differential expression data in conjunction with relationships asserted in the database.

The invention also contemplates use of drug discovery targets for drug discovery. How to use drug discovery targets identified through the use of the invention (optionally following further validation) in drug discovery will be apparent to persons of ordinary skill in the art. A typical means includes screening a diverse library of compounds against the target and using knowledge gained thereby to iteratively design and screen new compounds having greater potency.

Analysis of Microarray Expression Data

The following provides examples of how a KRS may be used in conjunction with user-provided differential gene expression data to analyze, understand or validate candidate drug discovery pathways according to the principles of invention. This detailed description of preferred, exemplary embodiments of the invention, like the preceding description, is intended for illustrative purposes only and is not limiting on the invention. Rather, the limitations of the invention are set forth in the appended claims.

Figure 3:
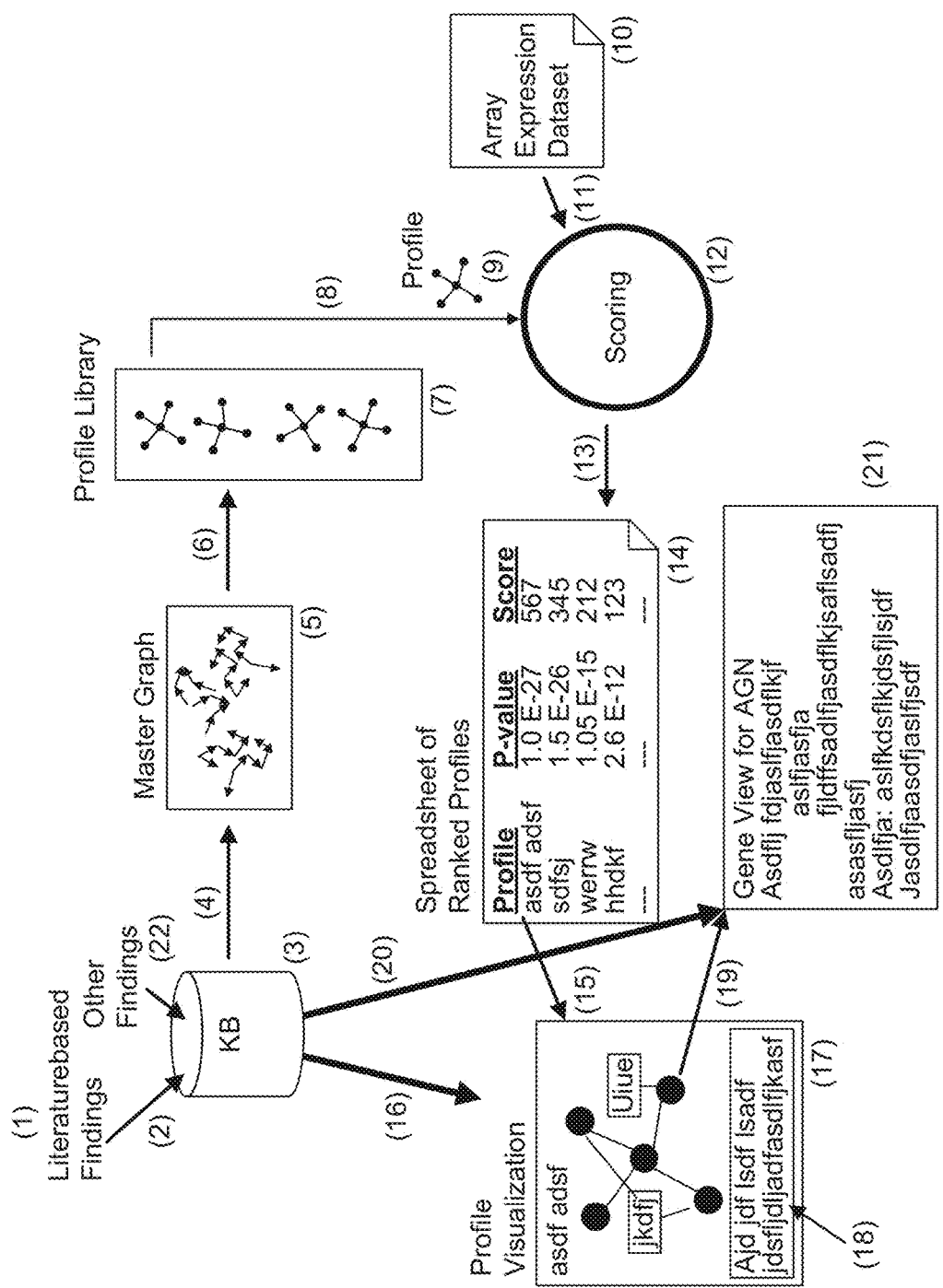
FIG. 3 is a schematic illustrating a method for analyzing gene microarray expression data according to a method of the invention.

An example of a process flow for analysis of microarray data in accordance with the invention is illustrated in FIG. 3. A knowledge base (KB) (3) including structured scientific findings taken from the research literature (1) and from other sources (22), as discussed earlier, is stored in the Findings KB and are structured according to the ontology (embedded in 3). The ontology and Finding KB, which form the KB, are stored in a KRS, and can be retrieved and manipulated using an KRS Application Program Interface (API) and/or querying language, as discussed above.

FIG. 3 shows the conceptual components of the analysis. The data structures, algorithms, and software components used to perform the analysis may form a stand alone software tool or they may be integrated with an existing platform and/or suite of applications that are used to access information stored in the KRS. The analysis may include two steps. A first step involves a series of computations over a copy of the KB to identify profiles, and a second step that involves scoring these profiles against user provided data. In the following description and in reference to FIG. 3, an example of the analysis uses user-supplied expression array. A library (7) of profiles is preferably pre-generated, but in other embodiments profiles may be generated as needed. The nature of this group of profiles may vary considerably based on the goals of the analysis, as is explained in greater detail below. A pre-generated "library" of profiles, mapping an entire KB, may be preferred for the sake of performance—pre-generate all of these maps so that retrieving them later will be faster. The user-supplied data may include array data provided from a third party product, e.g., an Affymetrix GeneChip©, online service or proprietary database.

Profile Definition

A "profile" may include information about, and be defined according to concepts such as a particular combination of genes or gene products that appear to act in a biologically coordinated manner, e.g., form all or part of a disease related pathway, cells and/or cellular components, anatomical parts, molecular, cellular or disease processes, and the relationships between them. An overview of a preferred profile generation and profile-to-data scoring algorithm is presented below. However, before turning to this example, it is important to emphasize that a "profile" as used in this discussion refers to a subset of the data contained in the database that is defined according to criterion(s) suited to the researcher's goals. As such, criteria (or a criterion) means any attribute of a profile that is determined, at least in part, by the researcher's needs. This may include criterion defined in terms of one or more biological concepts, the size of the profile (e.g., graph size), or the findings connectivity in the profile. It should therefore be remembered that the examples of profile criteria enumerated below are intended only as exemplary embodiments of profile defining criteria. In general, it is understood and indeed expected that profile defining criteria will vary from one application of the invention to another since a profile structure according to the invention is driven by research goals.

Thus, the effectiveness of one or more profiles in communicating information depends upon the criterion (or criteria) used to define the profile(s), which naturally depends upon the particular scientific goal for which information is being sought. For example, if it is believed that information relating to a particular cellular process would be highly informative of a targeted pathway, then findings relating to this cellular process would be a factor to consider when selecting a profile criterion. In another situation, the source of the findings (e.g., tissue type) or the size of the profile (e.g., the size of a graph structure illustrating the profile) may be effective profile selection criterion.

Profile Generation

Referring again to FIG. 3, step one, profile generation, begins with a pre-calculation that assembles one or more libraries of profiles from the KB. Each library contains all the profiles found in the KB that fit a certain set of criteria. The criteria may be pre-set by the system or defined by the user and may pertain to any category in the database, e.g., genes or gene products, processes, sources for findings, organism type, etc., or other criteria, e.g., limit number of nodes per profile.

Conceptually, each profile is a response to a query against the KB to find networks of findings that meet the criteria. The libraries may be pre-built to optimize performance, or the libraries may be built directly against the KRS, so as to allow libraries to incorporate recently discovered findings as they are stored in the KB. Profiles could also be built using something of a "bootstrap approach": an initial set of profiles could be built, then tested for sensitivity in detecting expression changes, and the best profiles could be enlarged (by adding more gene members, by merging profiles, or by otherwise changing the criteria that define the profile model), and the sensitivity test repeated. Eventually profiles that are optimal in detecting gene expression changes (the per gene-member sensitivity measure would be optimal) but not too large could emerge from this process.

The profiles are generated by first extracting a subset of the KB findings (4) and then converting findings (4) into a large graph data structure (5). This is essentially a simplified version of the KB that is amenable to high-performance graph data structure operations. Part of this simplification may include converting findings from a literature-based representation, where each finding represents a result from a performed experiment, to a biology-based representation, where each finding represents a conclusion about biology.

The profile generation algorithm then processes this graph (6) to produce a library of gene-centric profiles (7) that match the input criteria. Examples of input criteria are the size of the profile (number of nodes in each profile), the processes involved (e.g., "activation+cleavage" or "phosphorylation"), and/or the source of a finding (e.g., only human cells).

Many such libraries can be pre-generated given a profile generation algorithm and a set of parameters. If the libraries are built upon a copy of the KB, they must be re-built when the KB changes (e.g. when new findings arrive) if the profiles are to be up-to-date. The libraries may also be dynamically built, i.e., as the KB changes. Either configuration is contemplated and considered within the scope of invention.

Many profile generation algorithms could be used. For example, a gene-centric algorithm may be used. In this embodiment, the algorithm creates one profile for each gene in the KB. Each gene's profile consists of the gene that "anchors" the profile and a set of "nearby" genes that match a certain criteria. By "nearby" it is meant those genes that are most directly related to the anchor (or "seed") gene through some process, in terms of the number findings linking the gene to the anchor gene. This approach is termed "model-driven" because the profiles are based on a pre-defined algorithmic model. Alternatively, a "data-driven" model may be used, where the profile is not pre-generated but instead is assumed to be the set of differentially regulated user genes together with their know interactions as revealed by the KB. This essentially takes all the user genes and connects them using findings from the KB.

Step two, Profile Scoring (12), is the process of computing a P-value that ranks a profile (9) against the expression data (10). The profiles are preferably pre-generated independently of expression data and are stored in a profile library. In a particular application, there may be many profile libraries generated, each of which contains profiles matching the user or system specified criteria. Profile Scoring described herein will work for any of these libraries. In one embodiment, the algorithm makes two simplifying assumptions.

1. The expression array data is converted into a list of dysregulated genes (11) (i.e., abnormally up or down regulated) by selecting only those genes that show an N-fold or greater difference in regulation (in one embodiment, N=2 or greater). This is a common initial simplification for expression analysis. However, in other embodiments a more sophisticated continuous distribution approach that uses the full distribution of expression values over all the genes in the experiment rather than a cutoff threshold may be used.
2. For the purposes of scoring, profiles are considered to simply be a particular set of genes from the KB, e.g., the aforementioned Findings KB. In particular, the relationships between these genes are not used for scoring purposes, only for the purpose of generating the profile and subsequently for display and annotating it during results creation (see below). Scoring algorithms may also take gene connections into account as well, leveraging directionality in the gene connections and/or the molecular process nature of the connections to score the "fit" between the profile and expression data set.

Several other embodiments of the invention are contemplated. In one embodiment, a continuous measure of dysregulation is used, rather than an expression level cutoff when comparing microarray data to profiles.

In another embodiment, one may develop an aggregate scoring metric that includes graph-theoretic metrics, either as a compound score or a coarser ranking for profiles that match based on the existing score. For example, for N profiles that score equally well using a first metric, rank them further based on, e.g., graph connectivity metrics under the assumption that the more connected the genes, more likely they are working together.

In another embodiment, the system could allow user annotation to indicate (hypothesized) dependencies within the expression dataset. Specifically, if users have a priori knowledge about dependencies between the genes in their experiment, allow this to be included (e.g. as edge annotations, additions of new edges, or removal of edges whose evidence is hypothesized to be weak) in the set of genes to be analyzed. This feature, which is preferred, would require that the analysis gene sets have edge drawings (if it is desirable to display this information in graph form) which use the same semantics of directness as those underlying the profile edges, i.e., a data-driven profile can be constructed from user-supplied information. Alternatively, forms may be provided to input edges and tables provided for visual output for the edges. Thus, in addition to findings from the literature, users can add their own findings, or modify existing ones by, e.g., specifying a confidence measure. These user findings could be modifications to the KB itself (add custom findings to the KB, which are then converted to the graph (5) format) or to the graph itself (convert KB→graph as usual, but then modify graph (5)). Updates to the KB may use templates to enter these new findings, as discussed above. If these findings are added to the graph, then templates customized for graph edits may be used. This resulting data or model driven profile (or profiles, if there is more than one hypothesized dependency for a gene set) may then be used to further rank existing profiles by, e.g., doing an isomorphism comparison with model-based profiles. Thus, in this embodiment, data- or model-driven profiles are ranked against both the prior knowledge asserted in the KRS and the user's personal knowledge assumptions about the data.

In another embodiment, profiles could be generated based on the KB and the expression data itself, without necessarily converting the expression data to KB findings. This would be a hybrid data-driven and model-driven approach.

Both of the above approaches (or any other graph theoretic) could be refined by increasing the semantics of nodes, edges, etc and refining the corresponding isomorphism algorithm to reflect the particular semantics of nodes. For example, an edge "type" comparison in the isomorphism calculation.

Expand the ranking notion to explain all dysregulated genes in the expression dataset rather than only those genes that are mapable. For example, if one only can map 10% of all dysregulated genes, score all profiles lower under the assumption that none of them will do a particularly good job covering the biology of the full set of dysregulated genes. A similar profile weight could be calculated by comparing the ratio of mappable genes in the entire expression dataset against the set of genes covered by the KRS in order to estimate the relative coverage of the KRS against a given expression dataset.

Given models of chains of reactions that may underlie the observed gene expression, one can determine which models best fit the data. One method to compute this is to permute the user-supplied dysregulated gene expression values thousands of times and estimate the P-value based on the proportion of randomized data trials that score as well or better than the observed data (ie. Monte Carlo simulations). These mechanistic models (pathways) can either be pre-specified by users or generated automatically by searching over the knowledge in the KB to find biologically plausible paths between causative events (eg. binding of a ligand to its receptor) and biologically relevant effects (eg. transcriptional activation of a gene). The highest scoring models are the ones most likely to explain the data given the computationally-available information and provide users with actionable hypotheses.

Take into account the context of a user's experiment to adjust relevant content in the computation (eg. what type of cell line did they use, whether they know that certain genes are knocked out or transfected in, etc.). This would allow one to score profiles based on how well they matched up against this background knowledge about the experiment.

Take into account medium-throughput data to refine expectations of what is 'normal' for different cells, what proteins potentially can interact, etc. This would provide a normalized baseline across various biological contexts and refine the sensitivity with which one can distinguish statistically significant results.

Results from the analysis may be presented to the user in various forms. In one embodiment, three types are presented:

1. The first is a list of profiles ranked according to a profile score (14), generated by calculating the P-value for each profile (13) in the library and sorting the resulting list. Each profile lists the gene central to the profile, and any genes from the expression dataset that also appear in the profile. Users can view this list and pick profiles that appear to be interesting to look at them in greater detail. This output may be viewed using a spreadsheet program.

2. The second is a profile diagram (17) for each of the profiles. These diagrams show all the genes from the profile and the key relationships between them in the form of a "circles and arrows" diagram. Different symbols, colors, labels, and positions are used to encode additional information about the profile which is extracted (16) from the KB. An example of such information is the subcellular localization of the gene product (information that can be stored in the KB but is not used for profile generation or profile scoring in a preferred embodiment). The diagram itself may be generated (15) using an open source/freely-available $3^{rd}$ party diagramming tool from AT&T Research called Graph Viz, The output may be a printout of a diagram or a web-accessible graphic (image file or Scalable Vector Graphics—SVG—file).

3. The third is algorithmic association of biological processes with pathway profiles (18). This step involves generating a description or summary of the biology manifested by a given profile by performing algorithmic analyses of the findings relating the genes in the profile. Conceptually this is analogous to automatically generating a set of labels or captions (18) that describe the molecular, cellular, organismal and/or disease processes that best represent the function(s) of the genes in this profile. For example, while many cellular processes may be involved in the various genes in the profile, "apoptosis" may stand out as statistically significant among them. This aspect of results creation is particularly powerful since it leverages the unique structure of an ontology. These process annotations—e.g., the most representative or highest scoring ones—may appear on the diagram itself, or may be supported by a more complete list on a separate page, or via a web display that supports iterative "drill down" to reveal additional details. The output may be a text printout, but may also be presented to the user in a GUI interactive form.

The results output may be delivered to the user online as part of an integrated site that makes available all related KB applications. This is advantageous because every piece of information generated in all of the outputs is based on concepts and findings stored in the KB, which can also be made available to clients located on a network (e.g., the internet) for purposes of interrogating the KB for more detailed information related to the profile summaries. Thus, embodiments of the invention can be tightly integrated with supporting content, for example by allowing "click-thru" and "drill-down" functionality to take users from the high-level profile summaries to the detailed supporting evidence. One example of such a network adapted for this use is Ingenuity's LifeSciences web site where users may click on a node representing a gene to take the user to a "GeneView" page for that gene.

Other types of results may be provided to the user:

Annotation of profiles with drug target information by visually highlighting those genes that are known drug targets (i.e. for which a targeting molecule has been found or created) or for which there is evidence that suggests that they may be good drug targets based on e.g. gene family membership. Drug target information may be integrated into the results by simply highlighting the genes on a profile diagram, or drug target information could be taken into account when scoring the profiles.

Similar annotations and scoring modifications could be based on unwanted side effects for the drug, tissue specificity (e.g. increasing the score of profiles where most of the genes are known to be overexpressed in the tissue in which the experiment was performed), or IP (e.g. scoring profiles based on the number of patented genes in the profile).

A more detailed description of the profile generation and scoring steps according to a preferred embodiment follows.

Pathway Profiles

As mentioned above, a first step of the analysis generates computational models for biological pathways. These models, referred to as "profiles", become tools for interrogating and interpreting genomic data sets like microarray expression data. They are constructed from findings in the KB, and consist of sets of gene (product) abstractions, together with their known macromolecular interactions, and various biological processes the KB asserts the genes to play roles in.

The gene abstractions consist of official LocusLink gene symbols to which are mapped known instances of gene and gene products in the KB, potentially from both human and non-human species. The intermolecular interactions consist of specific instances of effector gene (product)→object gene (product) relations; the mapping of gene (product) instances to the more abstract gene symbols thus allows inferred generalized effector gene symbol→object gene symbol relationships (as discussed earlier). Borrowing concepts from graph theory, the available genes and gene interactions can be represented computationally as collections of "nodes" (for genes) connected by directed "edges" (for interactions), with various properties being associated with each node (e.g. gene properties), and various properties associated with each edge (e.g. molecular process types, direction of process changes, number of findings/publications asserting the interaction, etc). In addition, various properties can be associated with the entire profile, including for example, biological processes, the number of genes in the profile, the method of construction, etc.

The ability to associate a rich set of node, edge, and graph properties with profiles provides opportunities to apply a variety of selection criterions on the profiles:

- Criterions applied during selection of nodes and/or edges can provide diversity in the composition and structure of the profiles produced.
- Criterions applied after profile construction but prior to scoring against expression data can reduce unproductive false 'hits' or provide a more focused analysis.
- Criterions applied after profile construction and after expression scoring can provide additional ranking of profiles (by criteria other than expression scoring) for review by researchers.

Profiles may be "gene centric" in nature: A pathway profile is constructed around each of the gene symbols in the KB, using each as a "seed" gene, and including other genes with which it is known in the KB to interact. In this way, the profiles come to represent the "interaction neighborhood" or "sphere of influence" of the seed gene. Profiles may alternatively be constructed using non-gene concepts as the "seeds". For example, a cellular process like Apoptosis could be selected as a seed, and then all or some subset of the genes the KB implicates in Apoptosis could be added to the profile, together with their known inter-molecular interactions (as edges). But regardless of the nature of the "seed" in the profile, the rationale behind profile construction about a "seed" is that if a particular profile can be significantly correlated with a genomic data set (e.g. expression data 10), then the "seed" becomes the focus of interpretation.

Algorithm for Pathway Profile Generation

Beyond the "seed" node and edges connecting the seed to other nodes, profiles may be constructed in a myriad of ways. All of these approaches attempt to deal with the following concerns: The complete set of macromolecular interactions represented by a KRS will usually be too large and too diverse to be compared in its entirety with a genomics data set. Hence, an algorithm is needed to "carve up" this large "macromolecular interaction space" into numerous practical-sized interaction neighborhoods to support a finer-grained probing of genomic data sets. This carving up should be done with considerable gene overlap among the different profiles to minimize the chance that a rare combination of genes might be missed. On the one hand, profiles should be modest in size so that the set of biological functions that might be ascribed to the profile are not too diverse or heterogeneous. Smaller size profiles also aid in human review and interpretation. On the other hand, profiles should be sufficiently large (i.e., they should include, e.g., a sufficient number of genes) so that there will be enough statistical power when computing correlations with genomic data sets and/or with biological associations, such as molecular, cellular, organismal, and/or disease processes defined in the KB (as discussed below). Another concern is that a profile should be relatively symmetrical in the collection of genes connected to the central "seed" gene. In other words, a highly interconnected "1st tier" gene (i.e., a gene connected directly to the seed) should not swamp the profile with 2nd-tier genes (i.e., genes one step removed from the seed) because this can change the seed-gene-centricity of the profile.

One example of an algorithm developed to address the above goals is referred to as a "spiral" algorithm. In this algorithm, profiles are generated from a fully-extended master graph (5) of all known interactions. Graph (5) is constructed from a complete set of the pair-wise macromolecular interactions held in the KB, and will naturally differ in density (i.e., connectedness among nodes) in different parts of it. For each gene or gene product concept represented by a node in the master graph:

1) Designate the gene or its product as the "seed" node.
2) Add all immediate neighbor nodes (genes known to participate in interactions with the seed gene) as long as the number of findings supporting the claim that the seed and the neighbor interact is greater than 1, or stop adding if the maximum number of nodes has been reached. The elimination of interactions based on only a single finding is thought to weed out unconfirmed or weakly-substantiated findings. These are the 1st tier nodes and the connections from the seed to the nodes are 1st tier edges.
3) For each 1st tier node, compile a list of nodes and edges (besides the seed) that are neighbors of the 1st tier node, as long as the number of findings supporting the interactions is 4 or more. This increases the stringency for scientific confidence in the interactions, which as explained above is consistent with assumptions about a decrease in the degree of influence of one gene over another when there are intervening genes between them. These additional nodes and edges are considered "2nd tier" candidates.
4) Sort the 2nd tier candidate edges by decreasing findings counts.
5) After all 2nd tier edge candidates have been enumerated and sorted by the findings count, begin adding 2nd tier candidates to the profile in a round-robin fashion, picking one 2nd tier edge candidate for each of the 1st tier nodes by selecting the 2nd tier edge with the highest number of findings.
6) Repeat the round-robin edge addition in step 5) until either the number of 2nd tier edge candidates is exhausted, or the maximum number of nodes for the profile has been reached. This results in a profile based on edges with the largest number of scientific findings substantiating the interactions.

The above "spiral" approach (essentially a breadth-first search of available nodes) aims to enlarge the profile in a symmetrical fashion. Second tier edges are added from 1st tier nodes with equal opportunity (but preferentially those with more findings counts), reducing the chance that a highly-connected 1st tier node (with lots of 2nd tier edges) will swamp the profile with its connections. Thus, the sphere of influence surrounding the seed gene is optimally represented. Additional profile assembly algorithms may also be used.

The above algorithm, when applied to each gene or product in the KB, results in a profile library where a model of each gene's sphere of influence is collected. Profile Libraries may be constructed which use specific edge types/ molecular process criterions [these criteria can be more general: can be based on cellular process types, disease states, etc] (e.g. binding only, functional interactions only, or all types) when selecting from available edges. Then, when analyzing a genomic data set (e.g. expression data set), each and every model in the profile library (or libraries) may be used to interrogate the data set, and the corresponding fit between the model and the data set is computed. This approach is referred to as "model-driven". As mentioned above, a fundamentally different, "data-driven" approach to profile construction may also be performed. In this case, the nodes from which the profiles are built consist of only those genes (or products) that are observed to be altered (e.g. dysregulated) in a genomic data set. When performed with data obtained from a time-series, interesting "spreading activation" patterns of profile enlargement can be seen.

Uses of the assembled profiles have focused on interrogating and interpreting large scale genomic data sets where the profiles are treated as static models. Additional uses of the profiles are also possible. For example, the pathway profiles could be fed to simulation software that could allow the dynamic behavior of the interacting genes to be explored. The process nature and directionalities (increases/decreases) of the inter-molecular interactions can be used to track "what if" scenarios regarding the changes (abundance) in one or more genes in the profile and the consequences of that change on the other members of the profile. Boolean networks and Petri nets offer some technologies that might be used in such simulations. Another example of how the pathways could be used is in the generation of testable hypotheses. Computational systems could be devised to generate experimentally verifiable predictions about the molecular interactions, and perhaps even report on reagents available (e.g. mouse knockouts in some of the profile's genes) and additional information for performing the experiments. There could also be computational support for the revision/fine-tuning of the profile models to reflect new knowledge obtained from those experimental verifications.

Pathway Profile Graphics & Biological Annotations

To facilitate understanding the gene composition, connectivity, and dynamics of pathway profiles, and how they overlapped with expression data patterns, a system according to the invention may be constructed to automatically annotate profiles with biological associations and render the profiles as interactive graphics.

Biological annotations consist of biological processes thought to be emergent properties of the set of interacting genes in the profile. These biological processes correspond to concepts defined in the Knowledge Base (KB), and can span different levels of biological abstraction/granularity:

Molecular processes, involving a macromolecule acting on another macromolecule

Cellular processes, involving a change in the state of cells

Organismal processes, involving a change in the state of an organism or organismal component Disease processes, involving an abnormal change in the state of an organism or organismal component The linked biological processes are those determined to be shared among a statistically significant fraction of the genes in a pathway profile. A "P-value" significance measure may be computed for each profile-biological process association to provide a means to rank different associations, and to flag particular associations as outstanding. The ranked list of biological associations can be presented to a user, together with lists of specific genes linked to those biological processes. In this way, a user is provided with biological "readouts" of a profile, which can aid in assessing the fit of the profile to the known biology of a tissue sample, or alternatively, reveal new insights about the biology underlying an uncharacterized tissue sample. In one embodiment, annotations are limited to biological process concepts; however, other embodiments of the system could leverage additional types of concepts in a KB (e.g. cell types, specific organs, increases/decreases in processes, and other combinations of biological concepts) to compute statistically significant associations for pathway profiles. Moreover, the system may be extended, or easily modified to include additional kinds of statistical analyses. A preferred algorithm for enumerating and statistically ranking the potential biological processes linked to a genomic data set is described below. Biological annotations of pathway profiles can occur either before or after the scoring of profiles against expression data. In the former case, the biological annotations can be used in pre-filtering the set of profiles based on biological criteria. In the latter case, the biological annotations can be used in ranking the various scored profiles according to biological weightings.

Graphical rendering of profiles aims to convert the extensively integrated information of a pathway profile into something that is quickly interpretable by a user. For example, genes (or gene products) in the profile may be rendered as nodes, and inter-molecular interactions are rendered as lines connecting the nodes. In both cases, labels accompany the renderings (nodes are labeled internally with gene symbols, and edges are labeled with molecular process abbreviations). The central "seed" gene may be graphically distinguished from other nodes (e.g., by using an octagon shape), and the protein structural class of each gene product may be conveyed by a unique node shape. The overlap detected between the expression data set and the genes in the profile may also be conveyed in the graphic as follows: dysregulated genes are labeled with their fold change (a + or − floating point value), and colored such that down-regulated genes are red, up-regulated genes are green, and the intensity of color parallels the magnitude of the dysregulation. Interactions between dysregulated genes may be highlighted visually by color and/or line thickness and/or line density and/or labeling of the line. All intermolecular interactions are preferably labeled with a series of single-letter abbreviations indicating interaction types, such as activation, deactivation, binding, transcriptional effects, modifications, cleavage, etc. This use of single-level abbreviations allows multiple processes to be summarized without creating over-crowded labeling. Lines connecting gene (or product) nodes may take the form of arrows, so that an "effector" gene is connected at the 'tail' end of the arrow, and "object" genes are connected at the 'head' end of the arrows. When reciprocal interactions exist between two genes (gene products), two arrows of reciprocal direction may be drawn between the gene nodes. Subcellular localization of the gene products may be conveyed by placing the gene nodes into labeled boxes corresponding to each of 5 main locations (nucleus, cytosol, cell surface, cell periphery, and unknown). The arrangement of the subcellular location boxes may or may not follow the convention of nucleus at the bottom, cell periphery and cell surface at the top, and cytosol and unknown in the middle of the graphic. Information about known or suspected drug targets are conveyed graphically using gene nodes that are highlighted in color and/or shape and/or labeling.

Using a ranked list of biological processes compiled as in the examples provided above, the top 3 or so most statistically significant biological processes may also be rendered as features on the profile graphic displays. For example, a biological process graphical feature may include a box containing the name of the biological process, the number of genes from the profile that are implicated in the process, and a computed P-value reflecting the statistical significance of the association with the member genes. In addition, the biological process box may be connected by dotted lines (to distinguish from intermolecular interaction lines which are solid) to those nodes depicting genes in the profile which the KB asserts are implicated in the biological process. Using an interactive GUI display of the profiles, the user may have an option to dynamically control the types and amounts of information conveyed. In addition, elements in the graphic profile display can be hyperlinked to detailed views into the KB for the concepts to which those elements correspond (e.g. a GUI summarizing all available knowledge about a particular gene).

The combination of extensive knowledge integration (connectivity, directionality, interaction types) within profiles, computed biological annotations, computer-generated graphical displays of the profiles, and superimposition of known pharmacological targets result in a system that can support rational strategies for drug target selection. The knowledge of connectivity and directionality of interactions among member genes in a profile can reveal the potential for information flow through the set of genes. The integrated knowledge regarding protein structural classes (drug target opportunities) as well as prior known drug targets (e.g., IP obstacles) can help in the selection of appropriate drug target candidates. The biological process annotations and connections to genes can help in predicting the biological consequences of modulating specific genes in the profiles. Taken together, topological knowledge, target candidacy, and biological consequences can support the selection and evaluation of novel pharmacological intervention strategies.

Algorithm for Computing Statistically Significant Biological Process Associations for Pathway Profiles The goal is to reveal biological phenomena from the KB that is associated with the collection of genes in profiles in a statistically significant fashion. Although the 20 or 40 genes in a profile are each likely to be associated with many biological processes, the ones of most interest are those that are shared by many of the genes. To be statistically significant, the shared biological associations should occur at a frequency that is higher than that expected by chance alone. Not only do we want to find these significant associations, we would like a measure of the significance of the association. This statistical measure of significance is called a "P-value". It is a probability measure (with values in the range of 0 to 1) that indicates the likelihood that the observed biological associations are simply due to chance. The lower the P-value, especially when below 0.05 (i.e. more than 95% confidence), the less likely the associations can be explained as mere chance events.

Let's assume that Profile X has 20 genes, and of those 20 genes 12 are known (from the KB) to be associated with the cellular process "migration". The question to be answered is: could the 12 out of 20 genes linked to "migration" be explained as simply reflecting the frequency of "migration" cellular processes among the set of genes in the entire KB, or is this concentration of "migration" genes unusual. To answer this question, you need to know the probability (p) that any randomly-selected gene in the KB will be associated with "migration". This probability can be determined by computing the distribution of KB genes across the various cell processes represented in the KB. This distribution may then be made available for quick access by the analysis software by storing the information in a database. In the case of the information available in the KB of a preferred embodiment, it was found that 386 genes are linked to the cellular process of "migration" out of a total of 10,500 genes in this KB. This means the probability that any randomly selected gene will be a "migration" gene is 386÷10,500 or 0.0368. The probability of 12 out of 20 randomly selected genes being linked to "migration" may be computed using the Binomial Distribution:

$$P(k) = \binom{n}{k} p^k (1-p)^{(n-k)}, \qquad (1)$$

where n is the number of randomly-selected items, k is the number of observed events of one kind, and p is the probability (frequency) of a single item being of the particular event. The $$\binom{n}{k}$$

term is "n Choose k" which is equivalent to:

$$\binom{n}{k} \equiv \frac{n!}{k!(n-k)!} = \frac{1}{k!} \frac{n!}{(n-k)!} \qquad (2)$$

From the example above, p would be 0.0368. From (1), and p=0.0368, we can calculate the probability that 12 out of a random selection of 20 genes would be linked to "migration" as:

$$P(12) = \binom{20}{12} 0.0368^{12} (1 - 0.0368)^{(20-12)} = 5.7567e\text{-}13 \qquad (3)$$

It is important to note that this computes the probability of exactly 12 genes out of 20 being linked to "migration". In judging the significance of this, we are interested in the cumulative probability of 12 "or more" genes out of 20. This is computed from (1) by summing the binomial probabilities:

$$\text{Significance} = \sum_{k=k1}^{n} \binom{n}{k} p^k (1-p)^{(n-k)}, \qquad (4)$$

where k1=12, n=20, p=0.0368.

For the "migration" cellular process, this gives the cumulative probability that any observation of 12 or more genes out of a profile of 20 occurring by chance of: 1.9e-12. This is the P-value, and in this case gives 1 in 1.0e12 chance that the results are due to chance.

This test is commonly referred to as the "Fischer Sign Test", and in the preferred embodiment is automatically performed on a profile for any of the cellular, organismal, and disease associations linked to the genes in the KB.

Scoring Statistics for Profiles

An example of an expression scoring statistical analysis based on profiles generated from the KB is presented next.

The following, generalized assumptions were made concerning this statistical analysis:
1. The knowledge base contains one or more findings about each of zero or more (KB) distinct genes.
2. Each of the generated profiles is a set of (BCP=Biologically Coordinated Pathway) genes from the KB
3. The user assays a set of genes (USR distinct genes).
4. The genes that the user assayed that map to the genes (MAP) is in the range [0,KB].
5. Genes that the user assays may be dysregulated (DYS), in the range [0,USR].
6. The significant genes are the ones that are dysregulated and mapped to the genes (SIG) which is in the range [0,MAP]
7. Some of the SIG genes may also be genes in a particular profile. For a particular BCP, this overlap (OVP) is in the range [0,min(BCP,SIG)]

Figure 4:
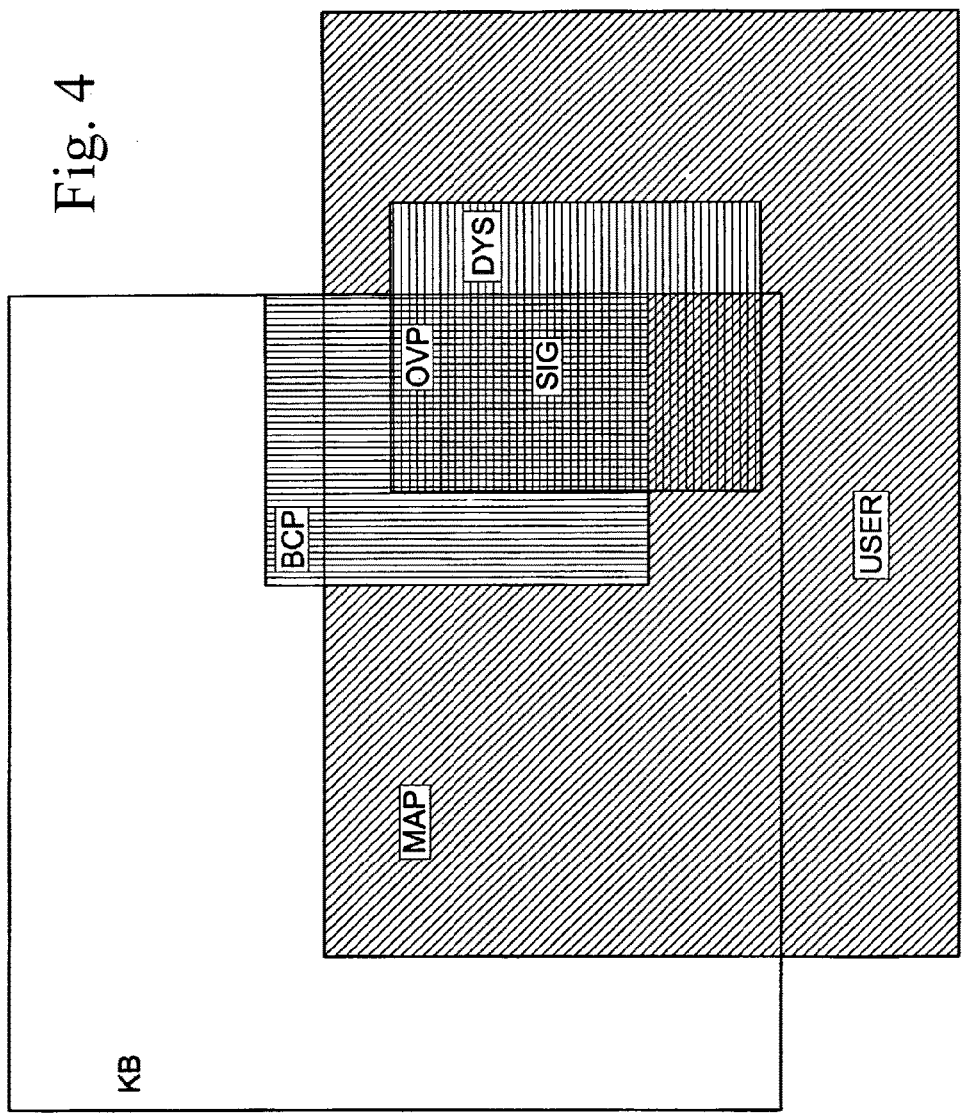
FIG. 4 is Venn Diagram illustrating a conceptual framework for determining whether a set or subset of user supplied gene expression data that is also present in a profile found in a Knowledge Base is statistical significant and therefore potentially related to an underlying biological process of interest.

FIG. 4 illustrates the relationships among the above sets in the form of a Venn diagram. The statistical approach described herein is concerned with determining whether an overlap (OVP) of some subset of a BCP with the SIG is statistically significant based upon the probability that OVP is a random event. Two possible approaches for determining this probability of randomness are presented Approach 1: Exact Probability of Overlap The initial approach calculates the exact probability of observing an overlap of size OVP given a fixed KB, MAP, BCP, and SIG. It computes what would be expected if the algorithm that generated the profiles randomly picked sets of BCP genes from the set of KB total genes (i.e., ignored all information we have about how the genes are related to each other, and blindly picked every combination of BCP total genes) and if the dysregulated genes in the assay are also random (i.e., every assayed gene has an equal probability of being dysregulated). The purpose of this statistic is to indicate how likely it is to observe the overlap if everything, both the matched profile and assay results, were completely random. So the closer the computed value is to one (100%), the more likely the overlap occurred by chance, and the closer the value is to zero, the better since 'random chance' as an explanation of how the overlap occurred (die null hypothesis) becomes less likely.

Note that whether there are 0 or 10,000s of USR genes that are not mapped (represented by the light green area in the USR gene box of FIG. 4) does not matter, since we have no knowledge about them; they are not in the universe of KB genes from which the profiles are picked. Likewise, only the genes that the user considers significantly dysregulated (DYS) that are mapped to KB genes matter, since if they're not mapped, we have nothing to say about them. However, the proportion of mapped dysregulated genes (SIG) does matter since we're also computing the likelihood that the particular dysregulated genes that overlap a particular profile happened to be blips—ie. not biologically coordinated. For the null hypothesis to be true, every combination of SIG genes that could be picked from the total MAP genes is equally likely. Treating the assay results as random makes the probability more robust since it does not assume the user's data is noiseless (averaging many repetitions of the experiment reduces noise, but often only a single microarray experiment is done for each condition/timepoint, resulting in significant undetected noise in the results) or that the genes that the user considers 'dysregulated' are actually biologically coordinated.

The formula for computing this exact overlap probability under the null hypothesis that both the profiles and dysregulated genes are random is:

$$P(OVP) = \left[\frac{\binom{KB-OVP}{BCP-OVP}\binom{OVP}{OVP}}{\binom{KB}{BCP}}\right]\left[\frac{\binom{SIG}{OVP}}{\binom{MAP}{OVP}}\right], \quad (5)$$

Where, again, the notation $$\binom{n}{K}$$

(or alternatively, "Choose (N,K)") refers to the mathematical operation (1/K!)*(N!/(N−K)!) for N, K integers. The first quotient enclosed within square brackets in Eq. 5 computes the fraction of the different profiles containing BCP total genes randomly picked from the KB total possible genes that also include the overlap OVP genes. The Choose (N,K) function computes how many distinct ways K items can be chosen from N total items (note that it evaluates to 1 if K=0 or K=N) without replacement (i.e., each item can only be chosen once—since the profiles are sets, the same gene appears at most once in each profile).

To visualize this, look at the conceptual framework diagram of FIG. 4. Imagine moving the BCP box (vertical lines representing one profile) around in the KB box (clear box, actually it is the constant proportion of the BCP box in the KB box that is relevant, not that it is a box). Each different location of the BCP box would be a different profile that could be randomly picked. Choose (KB,BCP) computes how many possible distinct combinations of BCP genes are possible. However, the OVP genes are fixed, so only some of all the possible random profiles would also contain the OVP genes. That's what the numerator calculates—how many different profiles consisting of BCP total genes that include the specific OVP genes could be picked randomly from all KB total genes.

The second quotient enclosed within square brackets in Eq. 5 computes the probability that the overlapping gene(s) are dysregulated but occurred by chance in the user's data. Suppose that only one mapped dysregulated gene (SIG) existed in a particular experiment, out of 1000 mapped user genes (MAP). The probability of P(OVP=1) would be 1/1000, since for an overlap of one, the overlap gene would have to be the single mapped dysregulated gene (ie. Choose (SIG=1, OVP=1)=1). However, there are 1000 ways a different single mapped gene could be chosen (ie. one way for each of the 1000 MAP genes). So there is a 1/1000 chance in this case that a single randomly chosen gene is dysregulated (SIG) and in the overlap (OVP).

Note that (Choose (SIG,OVP)/Choose (MAP,OVP))= ((Choose (MAP-OVP,SIG-OVP)*Choose (OVP,OVP))/ Choose (MAP,SIG)) in Eq. 5; the former was used above for simplicity, and the quotient appearing in the first square brackets can be rewritten equivalently. Both parts of the formula for P(OVP) assume a fixed set of overlap genes.

Multiplying the first and second bracketed quotients in Eq. 5 computes P(OVP), the probability that a given set of overlap genes would occur in randomly-chosen profiles (each containing BCP genes) and that the overlap genes happened to be randomly 'dysregulated' genes—the null hypothesis. For reference, the Eq. 5 simplifies to:

$$P(OVP)=(SIG!*BCP!*(KB-OVP)!*(MAP-OVP)!)/((SIG-OVP)!*(BCP-OVP)!*KB!*MAP!)$$

Some implications to keep in mind:
1. For a fixed number of KB genes and a fixed number of SIG genes:
   a. The larger the profile (>BCP), the MORE likely the match occurred by chance
   b. The larger the overlap (>OVP), the LESS likely the match occurred by chance
2. For a fixed number of OVP genes and a fixed number of BCP genes:
   a. The more dysregulated mapped genes (>SIG), the MORE likely the match occurred by chance
   b. The more genes we know about (>KB), the LESS likely the match occurred by chance
3. If BCP=KB, then if OVP is non-zero, P(OVP)=1 (ie. 100%)
4. If SIG=KB, then if OVP is non-zero, P(OVP)=1, since this means that every gene in the KB is a dysregulated user gene, so OVP=BCP for every possible profile
5. If MAP<KB, then P(OVP) in general is greater (ie. more likely to be random) than if MAP=KB In order of effect, the following parameters minimize P(OVP) the most (ie. reduce the chances the observed outcomes are random):
1. KB>>BCP (ie. Profiles only contain a small subset of all genes in the KB)
2. OVP>>1 (ie. The more dysregulated user genes that overlap the profile, the less likely it is to occur by chance)
3. MAP=KB (ie. All user genes are mapped to genes in the KB)
4. BCP=OVP (ie. Every gene in a profile is a dysregulated gene)
5. SIG=OVP (ie. All the mapped dysregulated genes overlap the profile)

Figure 5:
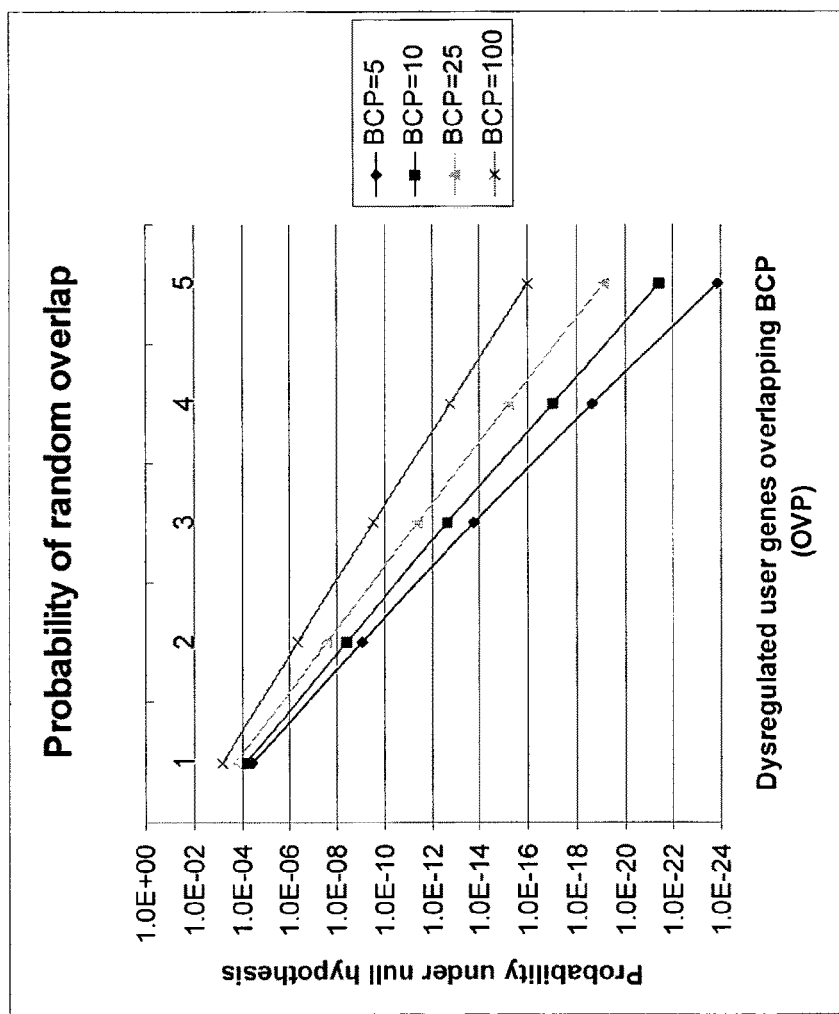
FIG. 5 is a graphical illustration of the statistical significance (as measured by the probability under a null hypothesis) that one, two, three, four or five user genes overlapping a profile from the Knowledge Base is a random occurrence.

FIG. 5 is a graph which shows the dominant effect (#2 above)—the greater the number of dysregulated user genes that overlap a profile, the less probable the overlap is to occur by random chance. Note that the y-axis is on a log scale, so each additional overlapping gene decreases the probability by several orders of magnitude. Note also that this effect is still dramatic even for larger profiles (ie. where the percentage of genes in the overlap as a fraction of total genes in the BCP is smaller). In this example, the values 7000 KB genes, 1500 MAP genes, and 70 SIG genes were used.

Keep in mind that although a profile with a large overlap may have a really low probability of occurring by chance, the value of the profile to a user depends not only on the low likelihood of being an artifact, but also on the explanation of how the genes in the profile are related to each other. The more believable the explanation of how the algorithm determined that the set of genes in the profile act in a biologically coordinated manner, and the more plausible that explanation is given the user's particular assay conditions, the more valuable the match, since it increases the probability that the decisions the user makes based on the insight provided by the profile explanation will be biologically sound.

Also note that this approach is computing the exact probability, which permits all profiles to be compared in relative terms against each other for a given KB and assay. However, this exact probability is not as good as measure for comparing best-scoring profiles across multiple assays, since the number of dysregulated mapped genes and maximum overlap, which have a significant effect on the exact probability value, can vary dramatically across experiments.

Approach 2: Cumulative Probability of Overlap (P-Value)

A preferred statistic for comparing overlaps across experiments, as well as getting a better intuitive feel for the significance of an overlap uses a cumulative probability distribution, instead of a single value from a probability distribution function (i.e., which is Approach 1). This can be computed by summing all of the individual probability values that are less than or equal to the exact probability value, and determining what fraction of the total sum of all the possible probability values it represents; this measure is usually called the 'P-value'.

Computing P-values over multi-variable distributions is usually complex. The typical approach is to fix as many variables as possible, determine whether the calculation can be reduced to an integral, and then solve the integral for the free variables. Note that: $0<=OVP<=BCP<=KB$; and $OVP<=SIG<=MAP<=KB$. So to make this calculation tractable, let us make the following assumptions:
1. When comparing P-values across experiments, the number of KB genes is constant. Since KB is already a large number, even if this assumption is not strictly adhered to, in general the difference will be minimal.
2. When comparing P-values across experiments, the number of mapped genes (MAP) is constant. This is less stringent than requiring that the user assay all of the same genes for each experiment, although presumably that would be the norm. Users only need to assay the same mapped genes with each assay; but if they compare general assay results to a targeted or different assay with only a fraction of the mapped genes in common, the P-value results would not be directly comparable.
3. The number of mapped, dysregulated genes (SIG) may vary across experiments (ie. $0<=SIG<=MAP$). However, for any given experiment it is assumed that the total number of SIG genes is non-random, although the particular SIG genes are assumed to be random.

Note that, unlike the familiar 'normal', one-dimensional bell-shaped distributions, this distribution is five-dimensional. Also, the probability density function (PDF) of this distribution decreases rapidly as OVP increases and is discrete (i.e., each dimension has integer ranges from 0 to a fixed number, not a real-valued range of –infinity to +infinity like the normal distribution). These features make it challenging to develop a formula that directly computes P-values; reducing it to three dimensions by requiring that KB and MAP are constant helps, but the integration (computation of the probability for each of KB*SIG*MAP possible outcomes) still requires a lot of CPU cycles (unless a closed-form integral exists that can directly compute the values). For this reason, it may be preferable to, e.g., pre-compute a table of probability values once, and then compare the probability value from the first approach to the tabular values for each BCP profile when determining a P-value. Nevertheless, if KB=10,000 and SIG is treated as a random variable, this lookup table could require about 100 GB of memory—a supercomputer. But if the total number of SIG genes is non-random, this calculation may be easily done once per experiment (i.e., so the same lookup could be used for scoring all profiles against it), which would require a lookup table with KB*SIG entries (KB since BCP size range is 1 . . . KB; SIG since OVP size range is 1 . . . SIG). This approach is preferred as it limits the demands on computational resources. For example, using this approach in the case where SIG=KB and KB=10,000, only a 100 MB lookup table would be needed.

The P-value is computed by summing all probability values that are less than or equal to the probability value computed by the first approach and dividing by the sum of all possible probability values. Note that since the outcomes most likely to occur by chance involve an overlap of one gene, for cases where the observed OVP is greater than one, the P-value will tend to be quite small. So unlike the normal distribution, where a P-value<0.05 is generally 'significant', a lower threshold is preferably imposed for this distribution. A metric that computes the percentage of all possible outcomes that are less than or equal to the observed probability value may be better for assessing profile scores for single experiments than by using a straight probability value, but would not be suitable for comparing across experiments since the weight (probability value) for each outcome may vary significantly.

Pathway Quality Attributes

The believability of a pathway expressed in a profile and its relevance to user-provided genomics data depends on (1) the ability of the KB to accurately represent characteristics of biological pathways, and (2) the extent to which any given pathway in the KB represents the true biological pathway underlying the user supplied data. These metrics are referred to as Pathway Quality Attributes (PQAs). The examples of profile scoring discussed earlier would fall under a Category 2-type PQA and the KB's degree of knowledge about a particular pathway contained in a profile model would correspond to a Category 1-type PQA.

Table 1 provides several examples of PQAs. Each row refers to a favorable attribute of a pathway in a profile. A pathway in a profile that has one or more of these favorable attributes may tend to reflect either the KB's ability to accurately represent a true biological pathway (Category 1) and/or the pathway's ability to explain the true biological pathway in the user data (Category 2). Referring to Table 1, PQA nos. 1-10, 13-15 and 18 refer to Category 1-type PQAs and PQA nos. 11, 12, 16 and 17 refer to Category 2-type PQAs. Under column heading "Attribute", the attribute type, or quality, is summarized and under the column "Description", there is an example (or examples) of how this attribute may appear in a profile, or be implemented as a profile model criterion.

TABLE 1

| | Pathway Quality Attributes (PQAs) | |
|---|---|---|
| | Attribute | Description |
| 1 | Contains tight sub-network of recognizable pathway genes | Assume three genes minimum to form a notion of a pathway. Want the profile to include a network of at least three highly-interconnected genes for the recognizable pathway (the more, the better). |
| 2 | Dysregulated genes mutually highly-connected in the network | Prefer sub-networks that have a large number of dysregulated genes, and prefer even more those networks where such genes are further highly-interconnected and dysregulated as a whole (profiles can contain both dysregulated genes - those that were active in the experiment - and non-dysregulated genes. This is a major benefit since these additions can provide additional insight not obvious from just the dysregulated genes). In general, prefer to see more dysregulated genes. Given 2 profiles that each have 20 genes, one may have 3 out of those 20 dysregulated, and the other will have 10 out of those 20 dysregulated, the latter is preferable. |
| 3 | Findings connectivity | Prefer high level of connectedness of sub-network of genes, where connectedness is measured by # of findings supporting a given relationship or edge (e.g., pick profile size of 4 nodes that have at least 5 findings connecting nodes or prefer profiles where all pairs of nodes (genes) are related by 5 or more findings on average). |
| 4 | Edge connectivity | Prefer high level of connectedness of sub-network of genes, where connectedness is measured by # of edges (e.g., if there are 4 nodes in a network, then require minimum of 3 edges connecting each node to other nodes). |
| 5 | Journal source connectivity | Prefer high level of connectedness of sub-network of genes, where connectedness is measured by # journal sources. |
| 6 | Finding quality believability | Prefer high level of connectedness of sub-network of genes, where connectedness is defined by canonical or high-confidence profile edges given preference. This refers to a preference for findings that come from content sources that are more trusted. For example, 1 finding from a review article may be considered as trustworthy as 5 similar findings from original research papers because the latter are more likely to be shown to be wrong over time. |
| 7 | Consistent cellular function | Prefer genes known to be involved in same cellular function (A → apoptosis and B → apoptosis then A⇔B). For example, a preference for genes known to be involved in same cellular function with same direction of influence (A → increase apoptosis and B → increase apoptosis then A ⇔ B, but A → increase apoptosis and C → decrease apoptosis does not relate A to C). |
| 8 | Preponderance of evidence towards specific pathway function | Generalization of attribute 7 across all genes in a profile, i.e., if you have an entire pathway where ALL genes are known to be involved in, e.g., apoptosis, then this is a highly favorable attribute. This features may be thought of as an extension of the "seed" concept to include a "seed process" or "seed function" as the central element of a profile. |
| 9 | Tissue consistency | Prefer genes consistent with studied tissue: either shown to be dysregulated in experiment, or known to be expressed in tissue being studied (for non-dysregulated genes). |
| 10 | Direct (physical interactions are more reliable/robust) | Prefer connections/edges that are supported by evidence of direct physical molecular relationship, as opposed to only high-level/cellular/disease type associations. Direct physical interactions are considered better |

TABLE 1-continued

Pathway Quality Attributes (PQAs)

| Attribute | Description |
|---|---|
| | because they describe an actual mechanistic molecular interaction rather than the higher level result of that interaction (e.g. symptoms of a disease) |
| 11 Consistent with experimental expression change pattern | Prefer profiles where profile description of regulation relationships and dependencies is consistent with KB finding expression directional effects. This attribute may be evaluated for expression changes provided as a time series or without (since array results show evidence of past cellular events as well). So if A - inhibits → B, and A is down-regulated, then you might expect to see B up-regulated. If your expression data shows this (A down, B up) then this finding is a potential explanation. |
| 12 Consistency with experimental expression levels | Prefer high aggregate magnitude of expression change (four 3-fold dysregulated genes are more interesting than four 2-fold dysregulated genes). Aggregation may be measured by, e.g., average, sum, absolute values, etc. |
| 13 Intermediate genes that don't appear tied into pathway function | Avoid genes in a profile that are not able to be linked to a process that is central to the other profile genes (i.e., if statistics suggest that 3 out of 4 nodes relate to process A, but the remaining node does not, then avoid including this node in profile). |
| 14 No findings or literature bias | Avoid connectivity metrics that may be biased by coverage in the literature, or the coverage of a particular group of biological concepts (e.g., a particular group of genes) in the literature during KB data acquisition. This bias may be accounted for by, e.g. a normalization based on an understanding of the scope of content coverage in the KB, or the scope of content (e.g., genes types) studied in the literature. |
| 15 One or more seed concepts for profiles | A "seed" approach to associating a pathway to a profile (e.g., a seed gene) is one of various ways in which a story or significance can be drawn out of profiles for users. This allows profiles to have e.g. one or more seed genes that are considered to be the most central to the profile function. Allow users to specify these seeds OR allow the system to pick them e.g. by iterating over all combinations of genes in the KB. While a seed approach to profile creation may be computationally useful, other attributes of a profile, which may not focus on the seed, may be equally insightful. |
| 16 Connectable to experimental context | Good if a pathway function is related to something to do with the experimental context because it can validate that you are "in the right space". |
| 17 Pathway function is relatable to research goals | Good if a pathway function is related to something with interesting implications on system/disease target being studied in the experiment. A pathway may be biologically accurate and be associated with several biological functions. The function that is closest e.g. to the disease being studied may be of more interest to a research than those that are true but incidental to the central research question at hand. |
| 18 Gene sensitivity to neighbors | Discriminate between findings/connectivity that suggest a high or low likelihood that a gene and its neighbors will influence each other's activities. Can normalize against excessively high or low influence genes. |

As will be appreciated by those of ordinary skill in the art, the examples of PQAs above, in addition to those discussed earlier, are informative of the possible scope of profile definition criteria that will allow the creation of profiles best suited for research goals. As mentioned earlier, the lists enumerated above are provided only as examples of possible profile criteria and should not be understood as limitations of the invention.

System Configuration

A system for practicing the methods of the invention need not be limited to a single entity, e.g., a private company, which, for example, builds and interrogates a KB for biological pathway information and provides the user interface for inspecting results. Rather, a system may be created as a result of combined efforts from one or more entities, which when combined (e.g., by a customer or through a systems integrator) provides a system capable of being used to practice methods of the invention. In the following, an example of how each of the tasks associated with developing components of this system is provided. Reference is made to a "Company A", "Company B", etc. These entities may correspond to public entities, private entities, public-private entities or a combination thereof.

Company A builds and sells a KB (possibly by acquiring content from 3rd parties or creating the content themselves. This endeavor could itself be split, i.e., one company could build the KRS software system, another could build the ontology, a third could build tools to enter data, and a fourth could use the preceding to actually enter the data (findings).

Company B, a data conversion/translation company, transforms the KB into a graph network.

Company C, an analyst or systems integrator company, figures out what profile characteristics are important for a set of users/customers.

Company D, software developers, build an algorithm that constructs profiles based on criteria provided by Company C.

Company E builds and/or sells visualization and browsing tools to view Company D profiles.

Company F, software developers, build an algorithm to rank the profiles against various experimental datasets. Company F1 could do it for expression data, company F2 for protein-protein interaction data, etc.

Company G, systems integrations, integrates all of the above into a system that takes expression data and predicts functional pathways based on scoring profiles built from the KB through the graph.

Company H, an analyst or systems integrator company, possibly in conjunction with company C, figures out what additional pathway information would be useful to users for interpreting the pathway. This could include characteristics identified by company C but that were not used by company D to create the profile. For example, a particular profile generation algorithm may not try to build profiles around a central biological process automatically, but users will still want to know what process(es) are more or less central to the profile.

Company I, software developers, build a second set of algorithms to calculate and/or display additional attributes of these profiles (for example, our process annotations).

Company J, a content company, manually enters existing pathways, replacing companies A-D, so that company G can now build/integrate a system that uses the same profile scoring algorithm, visualization, GUI, and attribute calculations, but uses them against manually created profiles rather than computer-generated profiles.

Company K, software developers, might help company J by creating a "pathway editor" software package that lets users create their own profiles by drawing pathway-like diagrams. This is "reverse visualization": draw the picture, and infer the biological relationships by seeing which circles are connected to which arrows, etc.

Although the present invention has been described in detail with reference to its preferred embodiments, it is understood that various modifications can be made without departing from the spirit of the invention. The appended claims are intended to be construed to include all such embodiments and equivalent variations. All publications, patent applications and patents mentioned in this specification are hereby incorporated as if each individual publication, patent application or patent was specifically and individually indicated to be incorporated by reference.

We claim:

1. A method for evaluating user-supplied genomics data, comprising:
    defining a profile model based on a profile definition criterion, wherein a profile in the profile model includes a subset of data contained in a structured database, the structured database comprising findings data, wherein the profile definition criterion comprises any of a combination of genes or gene products that form all or part of a disease related pathway, cells or cellular components, anatomical parts, molecular, cellular, or disease processes and relationships between them, a threshold profile size, findings connectivity metrics, or a combination thereof;
    building a library of profiles according to the profile model using the structured database, wherein the findings data of the structured database are structured according to predetermined, causal relationships among gene or gene products, the structured database comprising a knowledge base having a frame-based knowledge representation data model structured according to an ontology having slots and facets that define relationships between different instances in the ontology, and the structured database defining biological relationships that are at least one step removed;
    wherein building the library of profiled using the structured database comprises:
        querying the structured database to find networks of findings within the structured database that meet the profile definition criterion;
        extracting said networks of findings from the structured database;
        generating graph data structures based on said networks of findings thereby forming an initial set of profiles;
        performing a gene expression sensitivity test on the initial set of profiles;
        changing criteria of a subset of the initial set of profiles, based on said gene expression sensitivity test, thereby enlarging one or more profiles in the subset of profiles; and
        repeating the steps of performing a gene expression sensitivity test on the enlarged profiles and changing criteria of a subset of the enlarged profiles based on said gene expression sensitivity test, in a recursive manner, based on the profile definition criterion, wherein the repeating results in the library of profiles;
    receiving user-supplied genomics data;
    scoring each profile of the library of profiles against the user-supplied genomics data using a profile-to-data scoring algorithm;
    identifying one or more profiles in the library of profiles that have respective subsets of data that overlap at least a portion of the user-supplied genomics data;
    determining, for each such overlapped profile, whether the overlap with the user-supplied genomics data is statistically significant based on a computed P-value, wherein the P-value is a probability measure that indicates the likelihood that the overlap is due to chance; and
    presenting a list of one or more overlapped profiles determined to have a statistically significant overlap, wherein the list is ranked according to the P-value computed for each of the one or more statistically significant profiles,
    wherein each of the defining, building, receiving, scoring, identifying, determining, and presenting steps are performed by a processing system.

2. The method of claim 1, further comprising:
identifying genomics information concepts related to the user-supplied genomics data; and
pre-generating the library of profiles, wherein the library of profiles is built such that it contains a profile in the structured database for each of a plurality of genomic information having a genomic information type, wherein the profile is generated from said genomic information, with its associated genomic information concept as the profile definition criterion, according to the profile model.

3. The method of claim 2, further comprising:
converting findings from the knowledge base into the structured database, wherein the findings include data, from public or proprietary sources, used to build the knowledge base, and wherein the structured database comprises a graph data structure that associates genomic information concepts, from the structured database, that are related to each other as specified by the findings; and
wherein the querying of the graph data structure to pre-generate the profiles from the library of profiles is based on the profile definition criterion.

4. The method of claim 2, wherein the genomic information type is one of a gene, gene product, and biological process.

5. The method of claim 1, wherein the determining whether the overlap is statistically significant comprises:
computing a probability of the overlap as a function of information contained in the structured database.

6. The method of claim 1, wherein the user-supplied genomics data is differential gene expression data, the method further comprising:
- identifying a new use for a known therapy, wherein the gene expression data relates to a biological pathway affected by the known therapy;
- prioritizing candidate development compounds for further development, wherein the gene expression data relates to a target of one or more candidate development compounds, and giving higher priority to candidate development compounds on the basis of whether or not they are likely to result in an undesirable effect based on their involvement in other biological pathways as embodied in a profile; and
- identifying disease-related pathways, wherein a disease is a side effect of drug therapy, wherein the gene expression data relates to the target affected by the drug therapy and the other biological pathways that are also affected by the drug or the drug discovery target and that result in an undesirable phenotype are embodied in the profile.

7. The method of claim 1, wherein the user-supplied genomics data includes differential gene expression data relating to a disease state, the method further comprising:
- validating whether the differential gene expression data are genotypic markers for the disease state according to whether a database-asserted biological association related to the disease state, which is shared among a plurality of overlapped profiles, is statistically significant.

8. The method of claim 1, wherein the profile definition criterion further comprises one or more of a number of genes, organismal process, gene connectivity, edge connectivity, findings source type, experiment contex and tissue consistency criterion.

9. The method of claim 1, wherein in the steps of building the library of profiles, each profile is generated from a seed node.

10. The method of claim 9, wherein the seed node is one of a gene, gene product, biological process, and genomic data type.

11. The method of claim 1, further comprising:
- computing a statistical significance for a biological association in the one or more statistically significant profiles.

12. The method of claim 1, wherein the building the library of profiles further comprises:
- for each profile generated through the steps of building the library of profiles, selecting a node for the profile based on a number of similar findings in the structured database that link the node to a neighboring node.

13. The method of claim 1, further comprising:
- displaying information related to the one or more statistically significant profiles and genomics data using a graphical user interface (GUI).

14. The method of claim 1, further comprising:
- annotating the one or more statistically significant profiles with biological associations asserted by the structured database including one or more of a cellular process, molecular process, organismal process, and disease process.

15. The method of claim 14, further comprising:
- displaying the biological association using one of a graphical user interface (GUI) and a report.

16. The method of claim 14, wherein the annotating uses classification information found in the ontology.

17. The method of claim 1, wherein the determining whether the overlap of an overlapped profile is statistically significant further comprises:
- testing a null hypothesis over a discrete probability distribution, the distribution being a function of the database size, profile sizes, the user-supplied genomics data size, and expression values.

18. The method of claim 1, wherein the building comprises:
- generating a plurality of libraries of profiles, wherein each library of profiles corresponds to a different one of a plurality of profile definition criterions.

19. The method of claim 1, wherein the generating the graph data strictures further comprises converting said networks of findings into said graph data structures, wherein the converting comprises converting said network of findings from a literature-based representation, wherein each finding represents a result from a performed experiment, to a biology-based representation, wherein each finding represents a conclusion about biology; and
- wherein the changing the criteria of the profiles of the initial set of profiles further comprises changing the criteria of the profiles which meet a gene expression sensitivity threshold, by adding gene members to the profiles or merging one or more of said profiles.

20. The method of claim 1, wherein the library of profiles detect gene expression changes in terms of gene expression sensitivity of said profiles, wherein the performing of the gene expression sensitivity test on the initial set of profiles comprises testing the profiles for sensitivity in detecting gene expression changes by using a per gene-member sensitivity metric; and
- wherein the repeating the gene expression sensitivity test on the enlarged profiles further comprises repeating the gene expression sensitivity test using said per gene-member sensitivity, metric in a recursive manner until the profiles are enlarged such that the profiles reach a threshold ceiling of number of profile members based on the profile definition criterion.

* * * * *